(12) United States Patent
Cioanta et al.

(10) Patent No.: US 6,796,960 B2
(45) Date of Patent: Sep. 28, 2004

(54) LOW THERMAL RESISTANCE ELASTIC SLEEVES FOR MEDICAL DEVICE BALLOONS

(75) Inventors: Iulian Cioanta, Cary, NC (US); Jacob Lazarovitz, Hod Hasaharon (IL)

(73) Assignee: WIT IP Corporation, Southborough, MA (US)

( * ) Notice: Subject to any disclaimer, the term of this patent is extended or adjusted under 35 U.S.C. 154(b) by 66 days.

(21) Appl. No.: 10/136,605

(22) Filed: May 1, 2002

(65) Prior Publication Data

US 2002/0165521 A1 Nov. 7, 2002

Related U.S. Application Data

(60) Provisional application No. 60/288,774, filed on May 4, 2001.

(51) Int. Cl.[7] ....................... A61M 31/00; A61M 37/00; A61M 25/00; A61B 18/04; A61F 7/12
(52) U.S. Cl. .................... 604/103.01; 604/265; 606/27; 607/113
(58) Field of Search .......................... 604/27, 47, 93.01, 604/96.01, 101.05, 103.01, 103.02, 103.05, 103.06, 103.07, 103.08, 103.11, 103.12, 112, 113, 264, 265, 523, 524, 916, 919; 606/27, 108, 190, 191, 192, 194; 607/96, 99, 104, 105, 113

(56) References Cited

U.S. PATENT DOCUMENTS

| | | | |
|---|---|---|---|
| 1,690,995 A | 11/1928 | Pratt et al. ................... 606/192 |
| 2,849,002 A | 8/1958 | Oddo et al. .................. 128/325 |
| 4,327,736 A | 5/1982 | Inoue et al. ................. 128/349 |
| 4,417,576 A | 11/1983 | Baran ..................... 128/207.15 |
| 4,423,725 A | 1/1984 | Baran et al. ........... 128/207.15 |
| 4,435,590 A | 3/1984 | Shalaby et al. ................ 560/61 |
| 4,441,496 A | 4/1984 | Shalaby et al. .......... 128/335.5 |
| 4,498,473 A | 2/1985 | Gereg .................... 128/207.15 |
| 4,532,928 A | 8/1985 | Bezwada et al. ......... 128/335.5 |
| 4,540,404 A | 9/1985 | Wolvek ........................ 604/96 |
| 4,552,558 A | 11/1985 | Muto ......................... 604/100 |
| 4,559,945 A | 12/1985 | Koelmel et al. .......... 128/335.5 |
| 4,605,730 A | 8/1986 | Shalaby et al. .............. 528/357 |
| 4,608,984 A | 9/1986 | Fogarty ....................... 128/344 |
| 4,649,921 A | 3/1987 | Koelmel et al. .......... 128/335.5 |

(List continued on next page.)

FOREIGN PATENT DOCUMENTS

WO  WO0189619  11/2001  .......... A61M/25/10

OTHER PUBLICATIONS

PCT International Search Report, International Application No. PCT/US02/13586 dated Nov. 5, 2002.

*Primary Examiner*—Brian L. Casler
*Assistant Examiner*—Mark K. Han
(74) *Attorney, Agent, or Firm*—Ganz Law, PC; Bradley M. Ganz; James L. Wolfe

(57) ABSTRACT

Medical devices that are configured for insertion into a body lumen, such as the male urethra, are provided with one or more inflatable balloons having elastic sleeves, wherein each elastic sleeve is adapted to inflate in response to inflation of a respective balloon, and to deflate in response to deflation of the respective balloon. When a balloon is in a deflated condition, a respective elastic sleeve exerts a circumferentially compressive force against the balloon to cause a smooth, reduced cross-sectional profile of the balloon along an axial extent thereof. This smooth, reduced cross-sectional profile can facilitate passage of the medical device through a body lumen during both insertion and extraction of the medical device. A thin layer of fluid may be disposed between a treatment balloon and a respective elastic sleeve to facilitate heat transfer from a treatment balloon to a surrounding elastic sleeve or to administer a therapeutic agent to localized tissue.

15 Claims, 22 Drawing Sheets

U.S. PATENT DOCUMENTS

| | | | |
|---|---|---|---|
| 4,700,704 A | 10/1987 | Jamiolkowski et al. | 128/335.5 |
| 4,743,257 A | 5/1988 | Tormala et al. | 623/16 |
| 4,762,130 A | 8/1988 | Fogarty et al. | 128/348.1 |
| 4,941,475 A | 7/1990 | Williams et al. | 128/692 |
| 5,098,379 A | 3/1992 | Conway et al. | 604/51 |
| 5,112,304 A | 5/1992 | Barlow et al. | 604/96 |
| 5,116,318 A | 5/1992 | Hillstead | 604/96 |
| 5,171,297 A | 12/1992 | Barlow et al. | 604/96 |
| 5,181,911 A | 1/1993 | Shturman | 604/96 |
| 5,257,977 A | 11/1993 | Eshel | 604/113 |
| 5,290,306 A | 3/1994 | Trotta et al. | 606/194 |
| 5,295,959 A | 3/1994 | Gurbel et al. | 604/96 |
| 5,334,146 A | 8/1994 | Ozasa | 604/96 |
| 5,338,299 A | 8/1994 | Barlow | 604/96 |
| 5,342,305 A | 8/1994 | Shonk | 604/101 |
| 5,366,472 A | 11/1994 | Hillstead | 606/914 |
| 5,370,899 A | 12/1994 | Conway et al. | 427/2.3 |
| 5,476,476 A | 12/1995 | Hillstead | 606/194 |
| 5,478,320 A | 12/1995 | Trotta | 604/96 |
| 5,492,532 A | 2/1996 | Ryan et al. | 604/96 |
| 5,554,119 A | 9/1996 | Harrson et al. | 604/96 |
| 5,611,775 A | 3/1997 | Machold et al. | 604/53 |
| 5,613,979 A | 3/1997 | Trotta et al. | 606/194 |
| 5,620,649 A | 4/1997 | Trotta | 264/515 |
| 5,749,852 A | 5/1998 | Schwab et al. | 604/96 |
| 5,797,877 A | 8/1998 | Hamilton et al. | 604/96 |
| 5,797,948 A | 8/1998 | Dunham | 606/194 |
| 5,855,546 A | 1/1999 | Hastings et al. | 600/3 |
| 5,868,707 A | 2/1999 | Williams et al. | 604/103 |
| 5,868,719 A | 2/1999 | Tsukernik | 604/265 |
| 5,868,776 A | 2/1999 | Wright | 606/194 |
| 5,873,880 A | 2/1999 | Williams et al. | 606/108 |
| 5,876,374 A | 3/1999 | Alba et al. | 604/96 |
| 5,916,195 A | 6/1999 | Eshel et al. | 604/96 |
| 5,976,152 A | 11/1999 | Regan et al. | 606/108 |
| 6,171,338 B1 | 1/2001 | Talja et al. | 623/11.11 |
| 6,210,715 B1 | 4/2001 | Starling et al. | 424/489 |
| 6,217,548 B1 | 4/2001 | Tsugita et al. | 604/96.01 |
| 6,280,411 B1 | 8/2001 | Lennox | 604/103.05 |
| 6,328,711 B1 | 12/2001 | Guibert et al. | 604/103.01 |

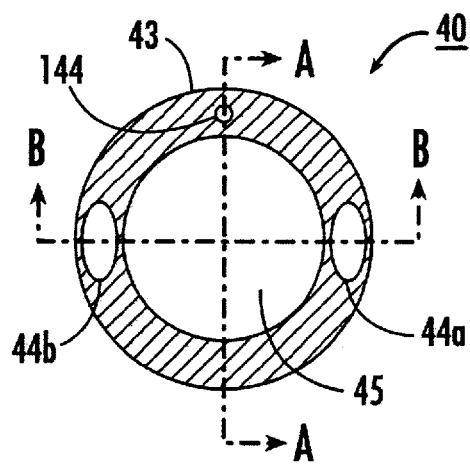
FIG. 4.
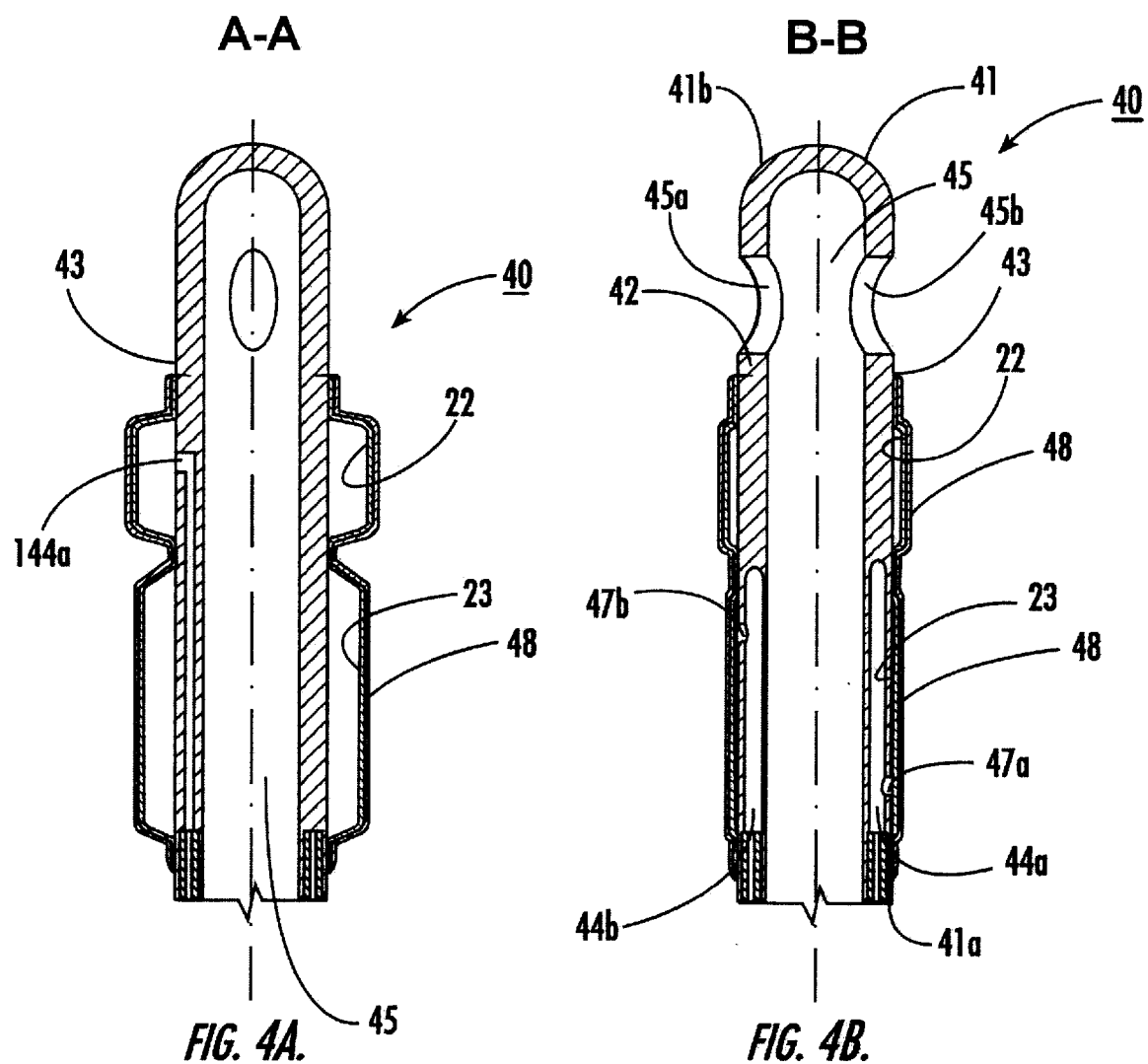
FIG. 4A.
FIG. 4B.

Set temperature: 60 °C
Sleeve durometer: 50A
Thicker sleeve (4 times) cured for 4 hours
Petroleum jelly between sleeve and balloon
Position: 1

Set temperature: 62 °C
Sleeve durometer: 50A
Thicker sleeve (4 times) cured for 4 hours
Petroleum jelly between sleeve and balloon
Position: 1

Set temperature: 60 °C
Sleeve durometer: 50A
Thicker sleeve (4 times) cured for 4 hours
Medication cream between sleeve and balloon
Position: 1

Set temperature: 62 °C
Sleeve durometer: 50A
Thicker sleeve (4 times) cured for 4 hours
Medication cream between sleeve and balloon
Position: 1

LOW THERMAL RESISTANCE ELASTIC SLEEVES FOR MEDICAL DEVICE BALLOONS

RELATED APPLICATIONS

This application claims priority from U.S. Provisional Application Ser. No. 60/288,774, filed on May 4, 2001, the contents of which are hereby incorporated by reference as if recited in full herein.

FIELD OF THE INVENTION

The present invention relates generally to medical devices and, more particularly, to medical devices configured for insertion into a lumen or cavity of a subject.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

BACKGROUND OF THE INVENTION

Several types of thermal treatment systems are known for treating certain pathologic conditions of the body by heating or thermally ablating targeted tissue. These thermal treatment systems have used various heating sources to generate the heat necessary to treat or ablate the targeted tissue. For example, laser, microwave, and radio-frequency (RF) energy sources have been proposed to produce heat, which is then directed to the targeted tissue in or around a selected body cavity. Thermal treatment systems have been used to thermally ablate prostatic tissue, as well as tissue of different organs. The term "thermal ablation" refers to exposing targeted tissue to a temperature that is sufficient to kill the tissue.

One particularly successful thermal ablation system is designed to thermally ablate prostatic tissue by a thermocoagulation process. In males, the prostate gland can enlarge and the prostatic tissue can increase in density resulting, unfortunately, in the closing off of the urinary drainage path. This condition typically occurs in men as they age due to the physiological changes of the prostatic tissue (and bladder muscles) over time.

To enlarge the opening in the prostatic urethra (without requiring surgical incision and removal of tissue), a conventional thermal ablation system employs a closed loop liquid or water-induced thermotherapy (WIT) system which heats liquid, typically water, external to the body and then directs the circulating heated water into a treatment catheter, which is inserted through the penile meatus and held in position in the subject undergoing treatment to expose localized tissue to ablation temperatures. The treatment catheter typically includes an upper end portion, which, in operation, is anchored against the bladder neck, and an inflatable treatment segment that is held, relative to the anchored upper end portion, such that it resides along the desired treatment region of the prostate.

In operation, the treatment segment expands, in response to the captured circulating fluid traveling therethrough, to press against the targeted tissue in the prostate and to expose the tissue to increased temperatures associated with the circulating liquid, thereby thermally ablating the localized tissue at the treatment site. The circulating water is typically heated to a temperature of about 60–62° C. and the targeted tissue is thermally treated for a period of about 45 minutes to locally kill the tissue proximate the urinary drainage passage in the prostate and thereby enlarge the urinary passage through the prostate.

Referring to FIG. 1, the anatomy of the male urethra 5, showing a thermal ablation treatment region 10 in the prostate 11, is illustrated. The thermal ablation treatment region 10 is indicated by the lined region in the prostate 11. For thermal ablation therapy, the treatment can be targeted to be carried out in a localized treatment region called the prostatic urethra 6, the treatment region 10 being generally described as the upper portion of the urethra from the prostate, which extends generally below the bladder neck 12a and above the verumontanum 11b of the subject. Alternatively, the treatment region 10 may include the bladder neck 12a or a portion of the bladder neck 12a itself.

FIG. 2A illustrates a treatment catheter 20 used in a WIT prostate treatment system identified as the Thermoflex® System available from ArgoMed Inc. of Cary, N.C. As shown, the treatment catheter 20 includes a bladder-anchoring balloon 22, a treatment balloon 23, and an elongated shaft 25. The catheter 20 is flexibly configured so as to be able to bend and flex to follow the shape of the lumen (even those with curvatures as shown in FIG. 2A) as it is introduced into the lumen until the distal portion of the catheter 20 reaches the desired treatment site. The catheter 20 is sized as an elongated tubular body with a relatively small cross-sectional area having a thin outer wall so as to be able to be inserted into and extend along a length of the desired lumen to reach the desired treatment site.

As shown in FIGS. 2B and 2C, the catheter 20 includes inlet and outlet fluid circulating paths 26i, 26o, respectively, as well as a urinary drainage channel 28 (which can also be used to deliver medicaments therethrough while the catheter 20 is in position in the subject). In operation, heated fluid or liquid, such as water or a water-based liquid, is heated external of the subject, directed into the catheter 20, and circulated in the enclosed fluid paths 26i, 26o in the catheter 20. The fluid is directed such that it travels through the catheter via the inlet path 26i to the treatment balloon 23 located proximate the desired treatment site and then back out of the treatment balloon 23 to the outlet path 26o, and then out of the subject. As shown in FIG. 2C, the circulating fluid is directed into the treatment balloon 23 which then expands in response to the quantity of fluid residing or traveling therein.

In operation, in order to anchor the catheter 20 in a desired position or location within the prostate 11 (after the catheter 20 is inserted into the prostate 11) through the urethra 5, the anchoring balloon 22 is inflated via a fluid (or other inflation media) introduced through the shaft 25 to the distal portion of the catheter 20 to cause the anchoring balloon 22 to take on an expanded configuration and reside against the bladder neck 12a of the subject (FIG. 1). Thus, when expanded, the anchoring balloon 22 is adapted to position the treatment balloon 23 in the prostate relative to the bladder 12. When deflated, the catheter 20, including the anchoring and treatment balloons 22, 23, can be removed from the urethra 5 of the subject.

For ease of insertion within and removal from a subject, it is desirable that catheters used for thermal ablation, particularly the anchoring and treatment balloons of such catheters, have a low, smooth, substantially constant profile during insertion and removal. Unfortunately, conventional anchoring and treatment balloons, when deflated, may not have a low profile and may have an irregular, non-smooth profile configuration. This may be particularly problematic in those balloons that are formed to take on a predetermined radial inflated shape, which they can retain even when asymmetrically compressed or pinched, in a manner that exposes a portion of the balloon to increased pressures. Exemplary anchoring and treatment balloons 22, 23 of a catheter 20 used for thermal ablation of prostatic tissue are illustrated in FIG. 3 in respective deflated configurations. The illustrated anchoring balloon 22 has plurality of "wings" 30 when deflated so as to provide sufficient material that creates an effective anchoring structure when the anchoring balloon 22 is inflated.

Unfortunately, the wings 30 of the anchoring balloon 22 may cause discomfort and/or irritation to a subject when inserted through a lumen or other body cavity, such as the male urethra. In addition, the treatment balloon 23, when deflated, has a diameter that is larger than the catheter shaft 25. The size of the treatment balloon 23 may also cause discomfort and/or irritation to a subject when inserted through a lumen or other body cavity, such as the male urethra.

SUMMARY OF THE INVENTION

In view of the above discussion, catheters and stents that are configured for insertion into a body lumen, such as the male urethra, are provided with one or more inflatable balloons having at least one elastic sleeve configured to encase or overlie the balloon(s). The elastic sleeve is adapted to inflate in response to inflation of a respective underlying balloon, and to deflate in response to deflation of the respective balloon. When a balloon is in a deflated condition, a respective elastic sleeve exerts a circumferentially compressive force against the balloon to cause a smooth, reduced cross-sectional profile of the balloon along an axial extent thereof. This smooth, reduced cross-sectional profile may facilitate passage of the catheter and/or stent through a body lumen during both insertion and extraction of the catheter and/or stent. In certain embodiments of the present invention, an elastic sleeve is configured as a unitary sleeve that extends over a plurality of underlying inflatable balloons.

Elastic sleeves, according to embodiments of the present invention, can retain their elasticity even after exposure to elevated temperatures, such as incurred during thermal or thermal ablation treatments so as to be able to collapse the underlying balloon to a configuration which presents a reduced or low profile (against the primary body) at the end of the thermal treatment.

Elastic sleeves that surround treatment balloons are configured to facilitate the transfer of heat, such as from heated fluid or other heated media, to tissue adjacent the sleeve. In certain embodiments, heat is provided to the tissue at a treatment region by circulating heated fluid in a closed loop system that includes the catheter. The heated liquid is held captured within the catheter and is directed to the treatment balloon that is positioned at the target site, and thus, the heat is transferred to the treatment region. In certain embodiments, the elastic sleeve has a thermal resistance such that a temperature drop through the elastic sleeve is no greater than about 2.5% and/or no greater between about 0.5 degrees and about 1.5 degrees (0.5°–1.5° C.) for a set temperature of about 60–62° C. when measured ex vivo.

According to other embodiments of the present invention, a thin layer of a material may be disposed between a treatment (or tissue molding or otherwise configured) balloon and a respective elastic sleeve. The material can be selected to facilitate heat transfer from a respective treatment balloon to the surrounding elastic sleeve. The fluid is biocompatible and may be one or a combination of, a gelatinous material, a cream, a material which transforms at the treatment temperature to another state (such as from solid to a liquid or from a viscous material to solid or which coagulates when exposed to a certain temperature), or a liquid such as oil (such as mineral oil or a cooking oil), saline, granulated solid or particulate matter such as salt crystals, or other materials such as hydrogels. Preferably, the material and elastic sleeve, together, have a reduced thermal resistance such that a temperature drop through the fluid and elastic sleeve is no greater than between about 1.5 degrees and about 2 degrees (1.5°–2°), and more preferably no greater than about one degree, and still more preferably, no greater than about 0.5–0.8 degrees when measured ex vivo.

In certain embodiments, the sleeve is configured such that with the material held therein, the externalmost surface temperature is greater than for corresponding sleeveless catheter configurations when measured ex vivo for catheters configured to transmit elevated or heated therapeutic temperatures to a subject. That is, the temperature is greater on the external surface of the sleeve of the catheter compared to the external surface of the treatment balloon on a catheter without a sleeve. In certain embodiments, the fluid is a viscous or semi-viscous medicinal or lubricant and/or biocompatible cream or gel such as a hydrocortisone cream or petroleum jelly or a vaginal or other intra-anatomical lubricant such as KY® jelly or a mixture lubricant/topical or local anesthetic such as LIDOCAINE. In other embodiments, a solid or particulate matter can be combined with one or more of the above fluids or materials. The solid or particulate matter can be selected for its ability to absorb or accumulate and distribute the heat through the sleeve.

Catheters and stents according to embodiments of the present invention may be advantageous because insertion and extraction into and from body lumens and cavities of a subject may be performed easily and with less irritation and/or pain to the subject. The sleeve can extend over one or more of the balloons used to mold or position the stent or catheter in the body. The sleeve can be chemically or mechanically attached to the underlying body such as with adhesives, ultrasonic or chemical bonding, friction fit, tied with sutures or string, and the like.

Certain embodiments of the present invention are directed to methods for thermally treating a natural body lumen or cavity. The method includes: (a) circulating fluid heated to above about 40° C. in a closed loop system that includes a catheter with a radially expandable treatment balloon and an overlying sleeve with a quantity of a selected material disposed therebetween; (b) concurrently expanding the treatment balloon and sleeve; (c) liquefying the selected material responsive to heat delivered from the heated fluid; and (d) directing heat to travel through the treatment balloon, liquefied material, and sleeve, responsive to the circulating and expanding steps so that, measured ex vivo, the temperature at the outer surface of the sleeve is above one degree less than the temperature at the outer surface of the treatment balloon on a corresponding sleeveless version of the catheter.

The present invention may find use for both veterinary and medical applications. The present invention may be advantageously employed for treatment of subjects, in particular human subjects. Subjects, according to the present invention, may be any animal subject, and are preferably mammalian subjects (e.g., humans, canines, felines, bovines, caprines, ovines, equines, rodents, porcines, and/or lagomorphs), and more preferably are human subjects. In addition, the medical devices can be used in different natural body lumens, including, but not limited to, the prostate, the cervix or uterus, veins and arteries, the sinus cavity, the throat or esophagus, the intestines, the colon, the rectum, and the like.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4 is a top cross-sectional view of a medical device (i.e., a stent or catheter) illustrating the center lumen or bore and associated passages formed in the walls of the device according to embodiments of the present invention.

FIG. 4A is a side cutaway view of the medical device of FIG. 4 taken along line A—A in FIG. 4. As shown, the medical device employs at least one respective elastic sleeve disposed around an anchoring balloon and a tissue molding and/or thermal treatment balloon according to embodiments of the present invention.

FIG. 4B is a partial side cutaway view of the medical device of FIG. 4 taken along line B—B in FIG. 4. As is shown, the anchoring balloon and tissue molding (and/or thermal treatment) balloons and corresponding sleeve(s) are in a deflated condition.

The graphs of FIGS. 10–15 are graphs of the temperatures measured (in experiments during which the catheter was evaluated ex vivo on the bench) at the externalmost surface of a catheter at six incremental axial positions about a line extending along the treatment balloon (either on the treatment balloon external surface or the sleeve external surface). Balloon surface point number 1 corresponds to the position closest to the distal or bladder end of the catheter with the other members corresponding to 2 mm spaced serial points therefrom. Positions 1 and 2 refer to the two radial positions which are aligned with one of the "in" or "out" liquid circulation holes inside the treatment balloon. Position 2 is only shown in FIGS. 10C and 11C. The circulating fluid was set to circulate with a temperature (set at entry into the catheter) of 60 degrees or 62 degrees Celsius ("the set temperature"). Certain of the figures correspond to a thicker sleeve while others correspond to a catheter with a thicker axial wall.

FIGS. 10B, 11B, 12A, 12B, 12C, 12D, 13A, 13B, 14A, 14B, 15A, and 15B correspond to temperature data for a catheter with a thicker treatment balloon thickness relative to FIGS. 10A, 10C, 11A and 11C. FIGS. 10A, 10B, 10C, 11A, 11B, 11C, 12A, 12B, 12C and 12D are graphs of temperatures for a catheter (with either the thicker or thinner treatment balloon thickness) without a sleeve and a catheter with a first sleeve thickness (a thin sleeve) positioned over the treatment balloon.

FIGS. 12A–12D are graphs which also show the temperatures when petroleum jelly was inserted between the catheter treatment balloon and the sleeve compared to temperatures of a catheter without a sleeve.

Figure 12A:
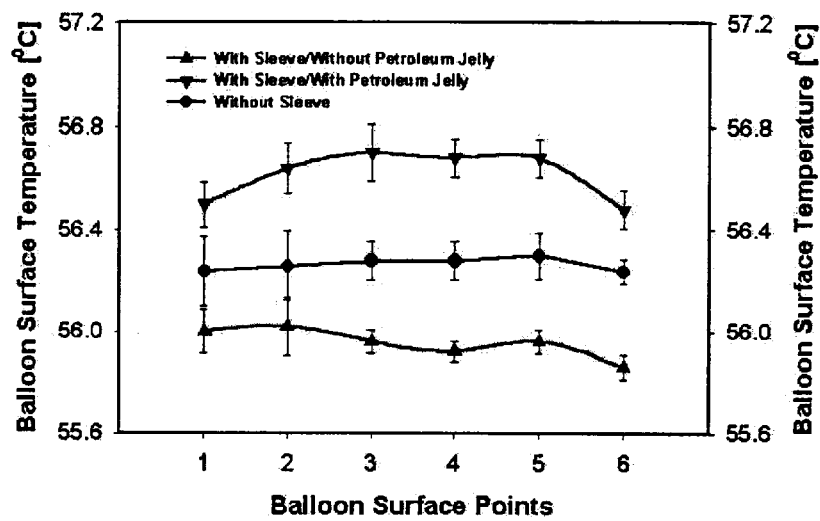
Figure 12B:
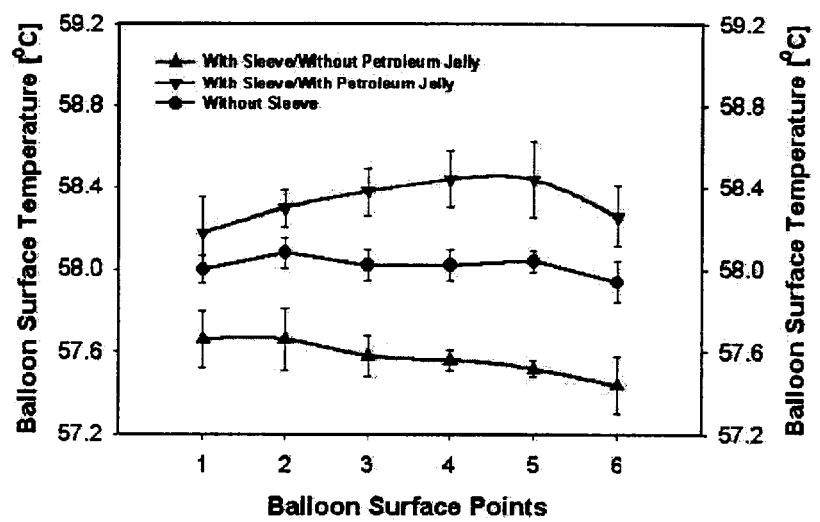
Figure 12C:
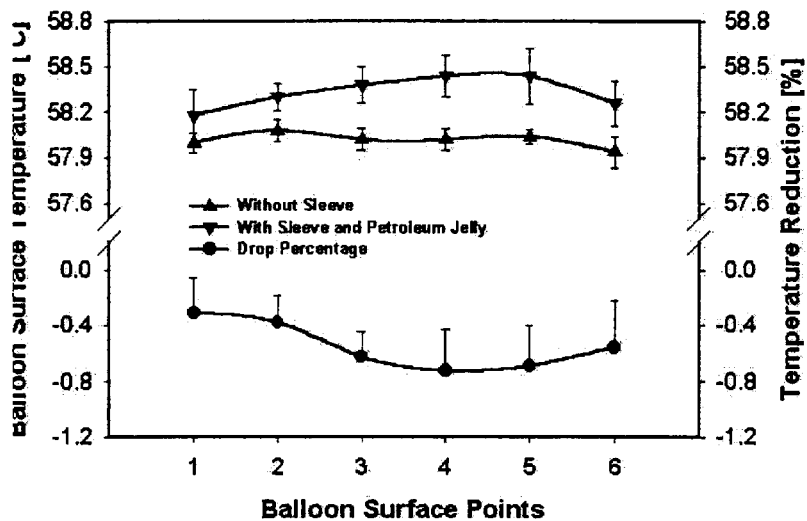
Figure 12D:
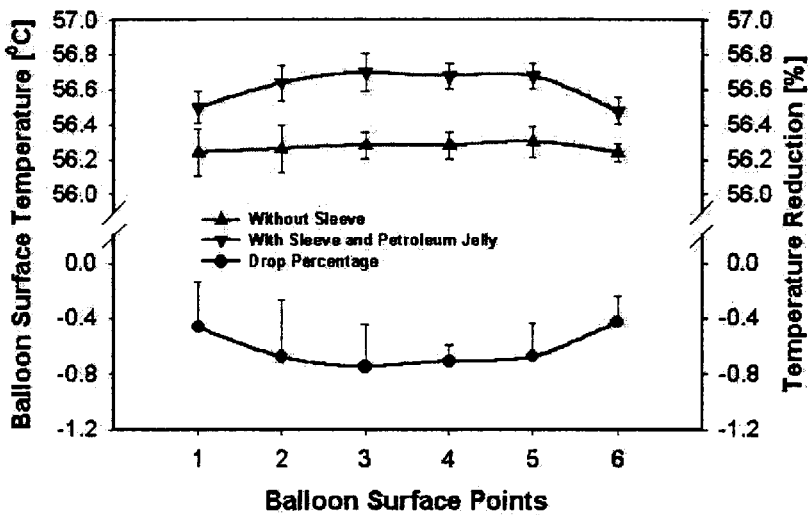
Figure 13A:
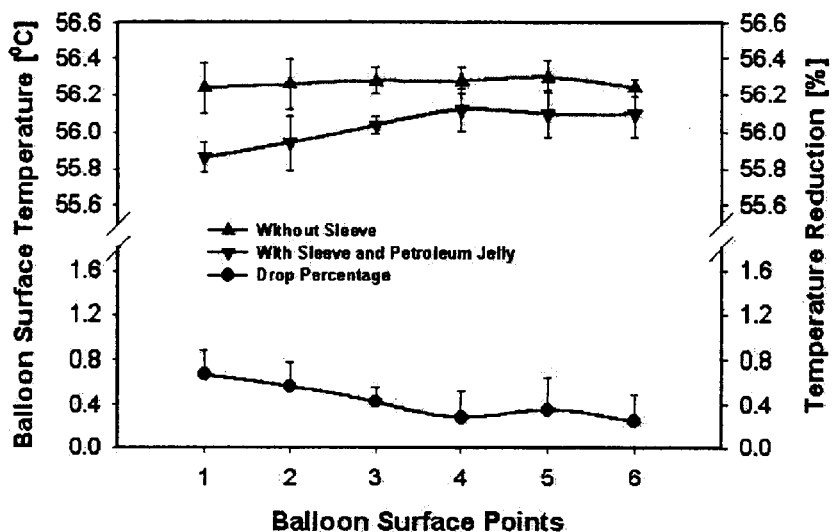
Figure 13B:
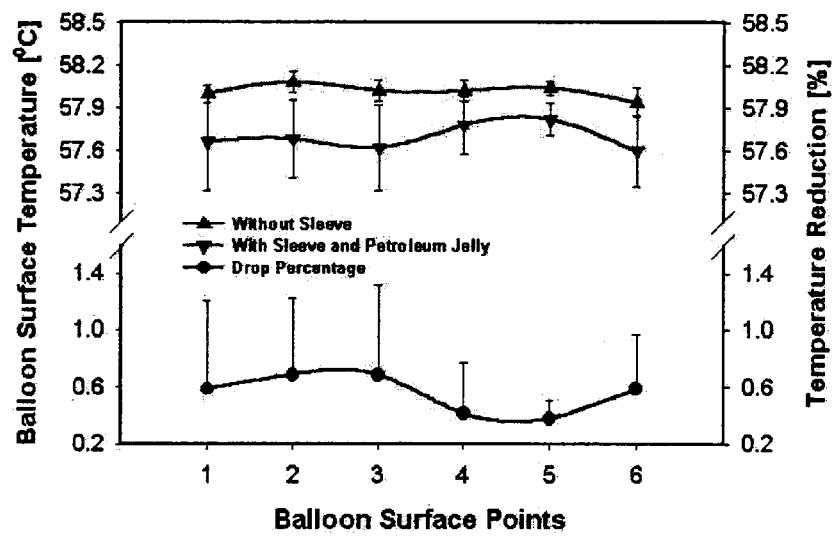

FIGS. 13A and 13B are graphs of temperatures for a catheter with a thicker sleeve (compared with that shown in FIGS. 10–12) and with petroleum jelly inserted between the catheter treatment balloon and the sleeve compared to a catheter without a sleeve.

Figure 14A:
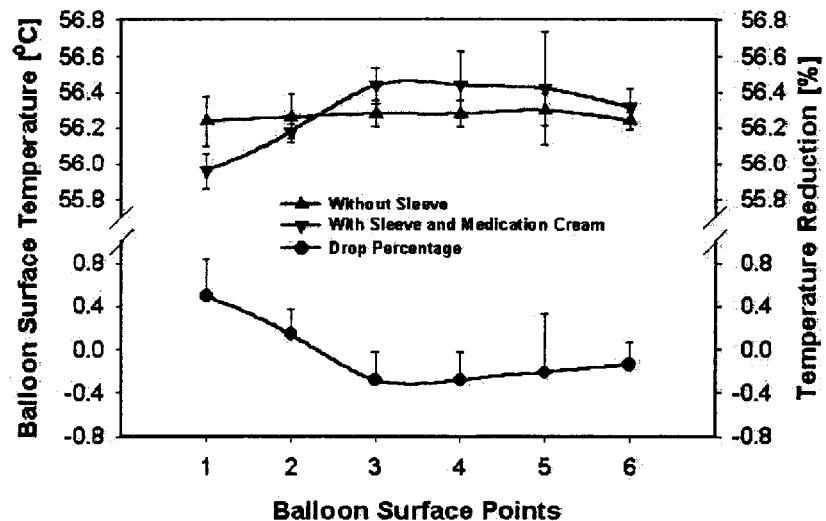
Figure 14B:
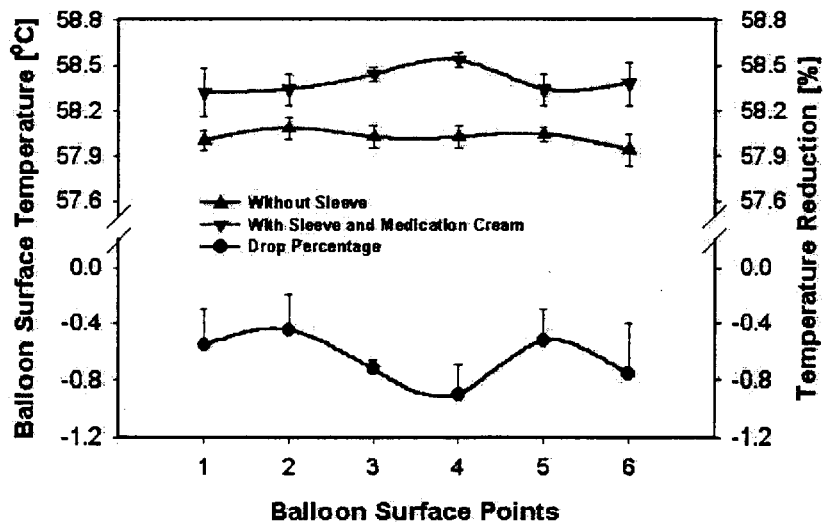

FIGS. 14A and 14B are graphs of temperatures for the same catheter and sleeve as shown in FIGS. 13A and 13B, but with a medication cream disposed between the treatment balloon and the sleeve.

Figure 15A:
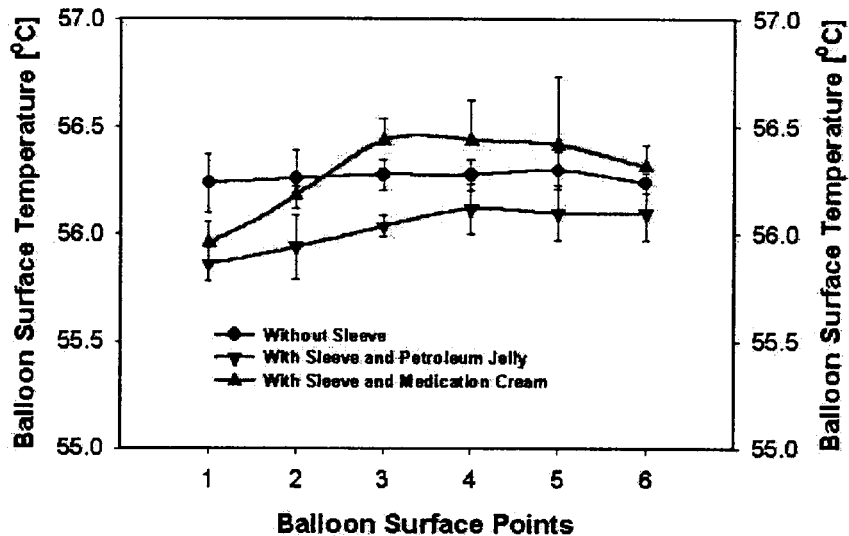
Figure 15B:
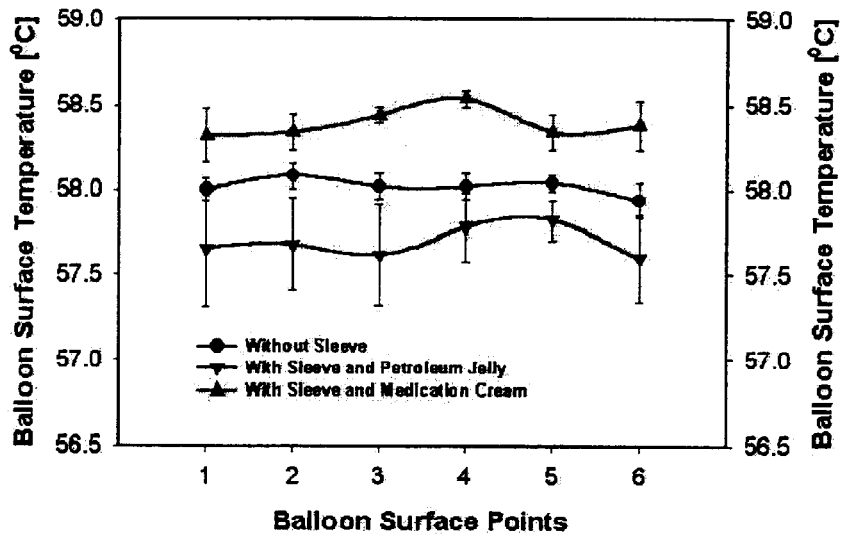

FIGS. 15A and 15B are comparative graphs of temperatures of the same sleeve configurations of FIGS. 13 and 14 illustrating the temperatures obtained with the thicker sleeves, the thicker wall treatment balloon and the two types of substances shown in FIGS. 13 and 14.

DETAILED DESCRIPTION OF EMBODIMENTS OF THE INVENTION

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will convey the scope of the invention to those skilled in the art. In the drawings, the thickness of layers, components or regions may be exaggerated for clarity. Like numbers refer to like elements throughout the description of the drawings.

For ease of discussion, medical devices (e.g., catheters, stents) according to embodiments of the present invention will be primarily discussed for use in the male urethra. However, catheters and stents according to embodiments of the present invention may be alternately configured (such as with balloons positioned at alternative locations about the length of the body (i.e., at the distal end) and/or otherwise adapted) as appropriate for insertion and use in other natural lumens or body cavities such as, but not limited to, the rectum, the colon, the uterus, the cervix, the throat, mouth or other respiratory passages, the ear, the nose, blood vessels, the lumens of the heart, and the like.

Figure 1:
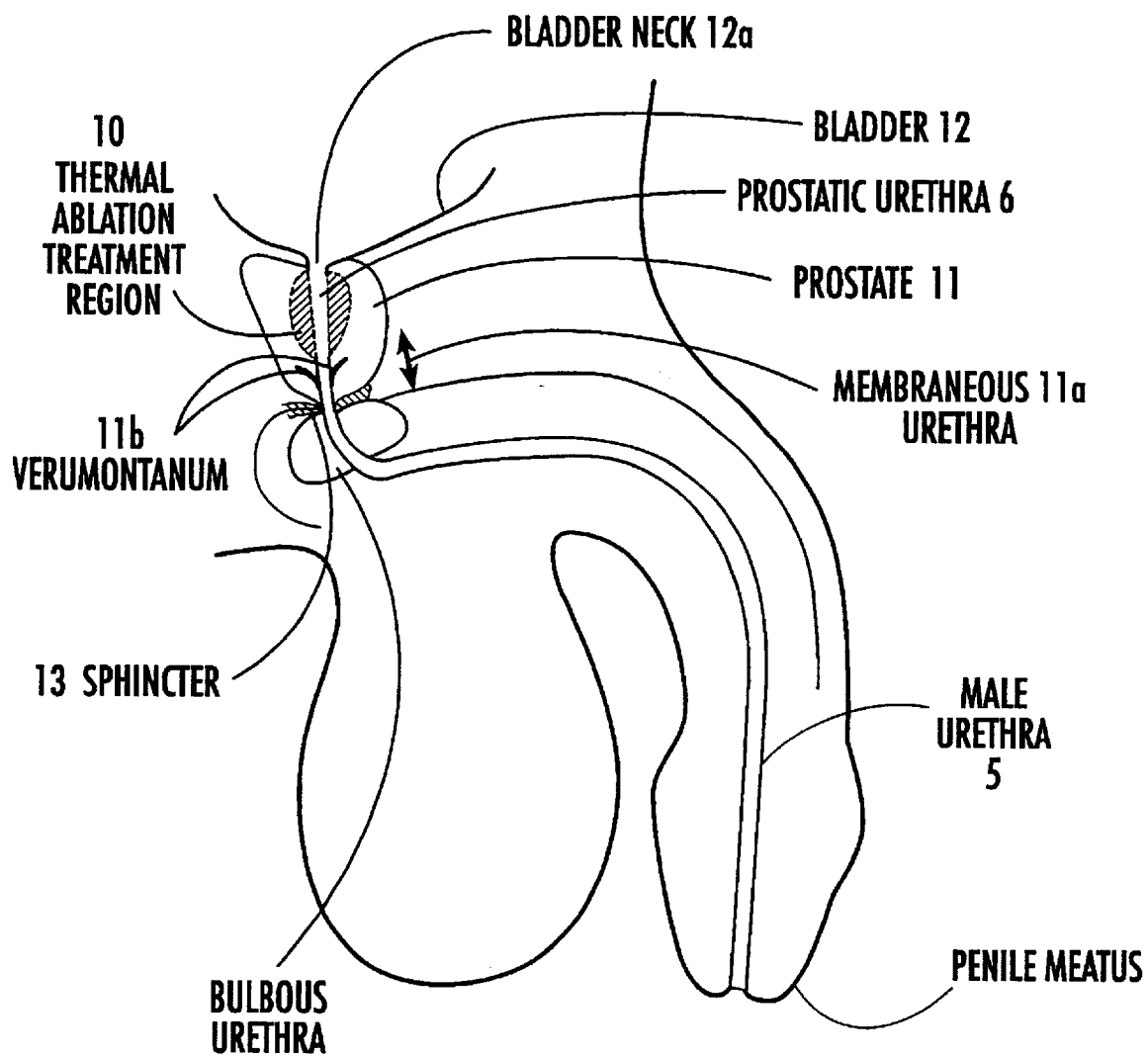
FIG. 1 is a schematic illustration of the anatomy of the male urethra showing a thermal ablation treatment region in the prostate.
Figure 2:
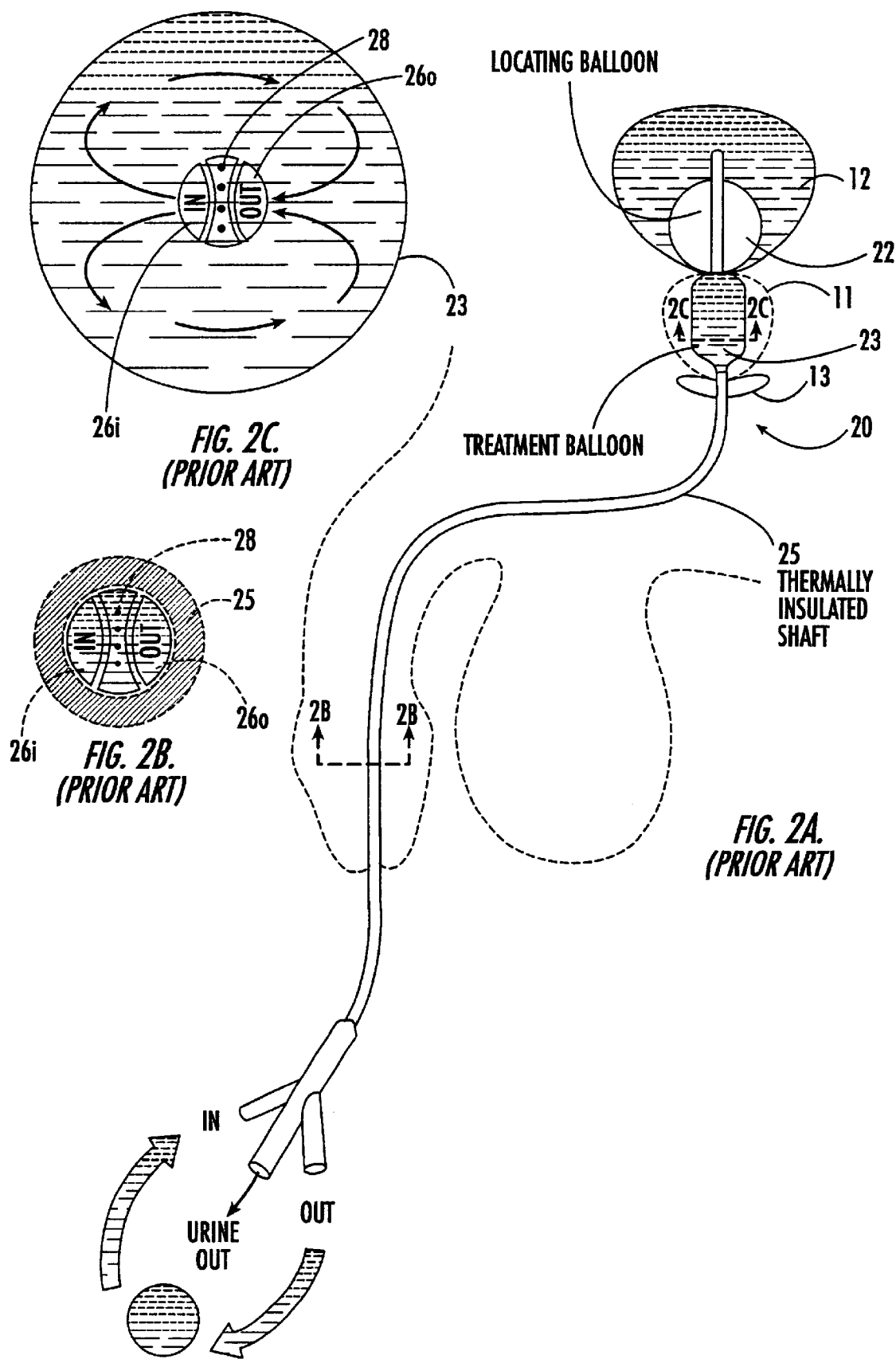
FIG. 2A is a schematic illustration of the prostate portion of the male urethra illustrating a prior art treatment catheter in position in a subject for delivery of thermal ablation treatment.
FIGS. 2B and 2C are enlarged section views of the prior art treatment catheter shown in FIG. 2A, taken along lines 2B—2B and 2C—2C, respectively.
Figure 3:
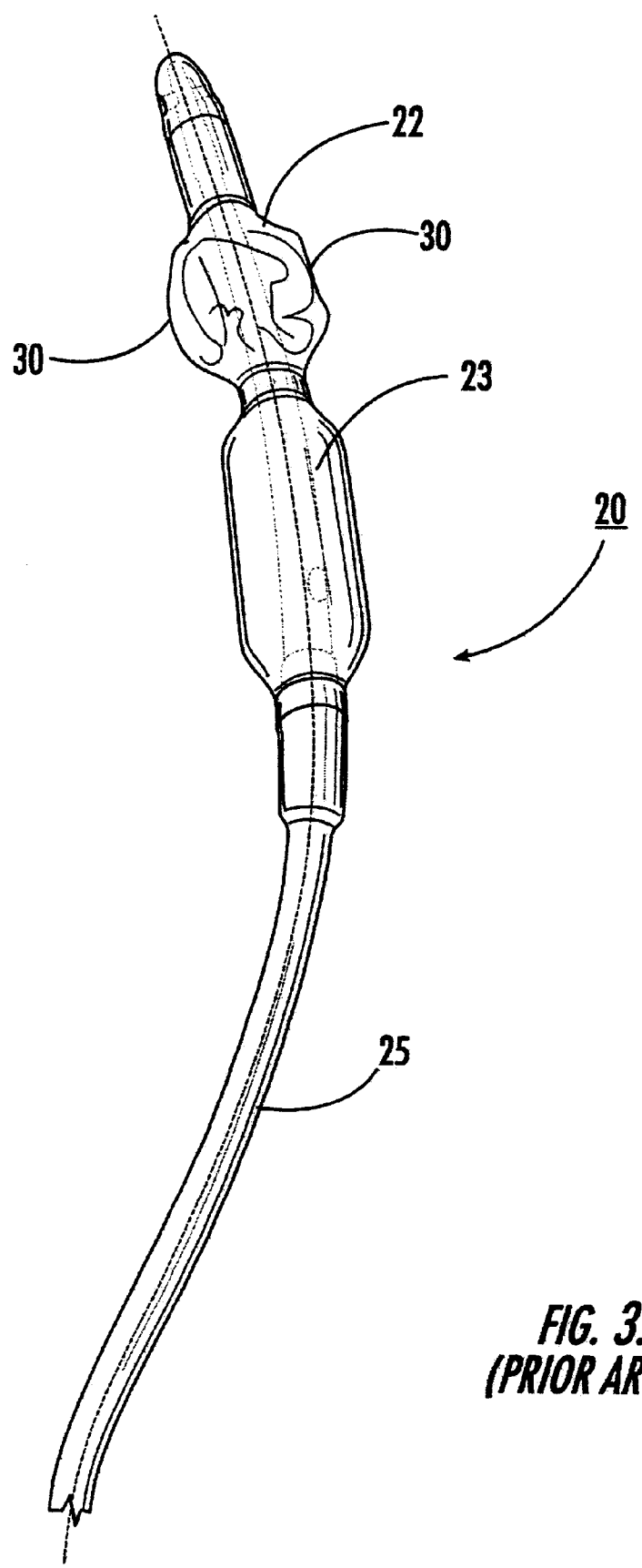
FIG. 3 is a perspective view of a prior art catheter used for thermal ablation of prostatic tissue wherein the anchoring and treatment balloons are in respective deflated configurations.

FIGS. 1–3 were discussed in the background section above. Referring now to FIGS. 4 and 4A–4D, a medical device 40 (preferably a stent or a catheter) is configured for insertion into a body lumen. The medical device may be configured for insertion into the male urethra to deliver thermal treatments (including heating, cooling, and thermal ablation treatment of tissue), according to certain embodiments of the present invention. The illustrated medical device 40 includes a flexible elongated tubular body 41 that has an outer wall 42 with an external surface 43. A pair of fluid lumens 44a (shown as the outlet passage), 44b (shown as the inlet passage) extend axially through the tubular body 41 from a proximal end 41a to a distal end 41b of the tubular body 41. The fluid lumens 44b, 44a serve as inlet and outlet fluid circulating paths, respectively, for a heated fluid (or other heated media) used in ablation treatment, as described above. In addition, the fluid or media within fluid lumens 44a, 44b may also serve to inflate one or more inflatable balloons as described below.

In the illustrated embodiment, an inflatable treatment balloon 23 is peripherally mounted to the distal end portion 41b of the tubular body and is in fluid communication with the fluid lumens 44a, 44b via respective ports 47a, 47b. As shown, the inlet port 47b can be positioned axially above the outlet port 47a. A urine drainage passageway 45 extends axially within the tubular body 41 and is configured to be in communication with the bladder 12 (FIG. 1) of a subject via apertures 45a, 45b, as would be understood by those of skill in the art.

Figure 4C:
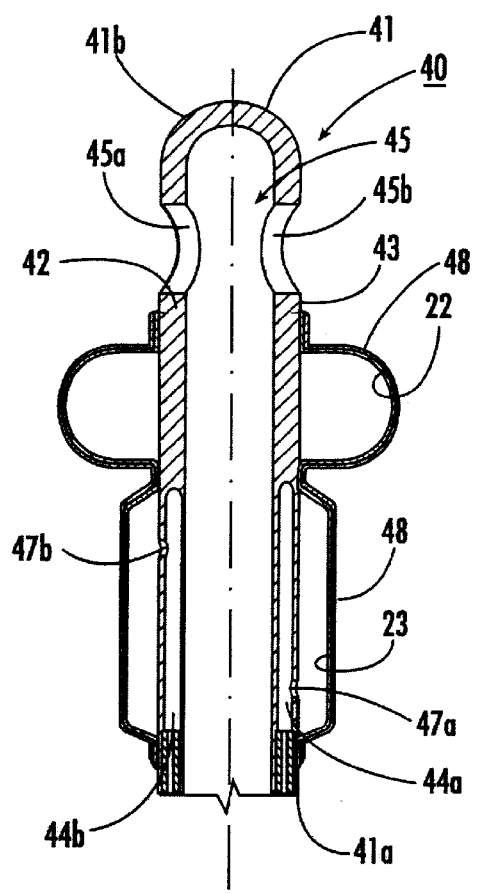
FIG. 4C is a side view illustrating the anchoring balloon and tissue-molding (and/or thermal treatment) balloon and corresponding elastic sleeve in inflated conditions.
Figure 4D:
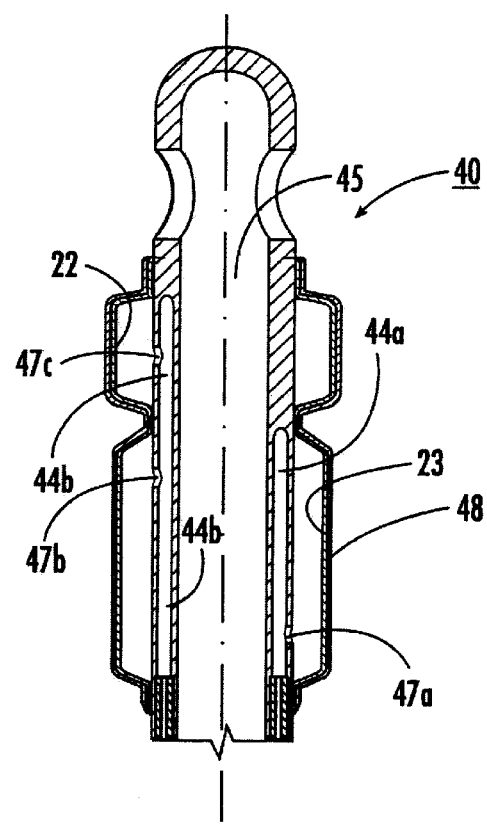
FIG. 4D is a partial side view of a medical device similar to that shown in FIG. 4B, but with the anchoring balloon and treatment/tissue molding balloon configured to be in fluid communication (and concurrently inflatable).

In the illustrated embodiment shown in FIGS. 4–4D, an anchoring balloon 22 is peripherally mounted to the tubular body distal end 41b at a location more distal than the treatment balloon 23. The anchoring balloon 22 is configured to inflate radially outward from the outer wall external surface 43 when fluid or other inflation media is provided thereto, as would be understood by those of skill in the art (see FIG. 6).

FIG. 4 and FIG. 4A illustrates that the device 40 may include at least one inflation path 144 which extends along an axial length of the body of the device to the anchoring balloon 22. The inflation path 144 includes a port 144a which, in operation, directs the inflation media through the inflation path 144 and to the anchoring balloon 22 to cause it to inflate. As such, the anchoring balloon 22 may be in fluid isolation from the treatment balloon 23 such that it is independently inflatable.

Alternatively, as shown in FIG. 4D, the fluid inlet channel 44b may be configured to extend axially a further distance with a port 47c disposed to be in fluid communication with the anchoring balloon 22 such that the treatment and anchoring balloons 23, 22, respectively, are in fluid communication and concurrently expandable in response to the circulating fluid in the inlet channel 44b.

As shown by comparing the deflated configuration of FIG. 4B with the inflated configuration of FIG. 4C, the treatment balloon 23 is configured to inflate radially outward from the outer wall external surface 43 when a heated fluid or other media is circulated therein. At least one elastic sleeve 48 surrounds the treatment balloon 23 and is secured to the tubular body 41 on opposite ends of the treatment balloon 23, as illustrated. The elastic sleeve 48 may be attached to the tubular body 41 in various ways including, but not limited to, chemical or mechanical means, such as with adhesives, ultrasonic or chemical bonding, frictional fit, physically tied with sutures, floss, or silk thread or string, and the like. The fluid or other media circulated within the fluid lumens 44a, 44b is preferably selected to be non-toxic and to reduce any potential noxious effect to the subject should a situation arise where the treatment balloon 23 integrity may be compromised, accidentally rupture, leak, or otherwise become impaired during service.

In certain embodiments, the elastic sleeve 48 is adapted to concurrently inflate in response to inflation of the treatment balloon 23 (FIG. 4C), and to deflate in response to deflation of the treatment balloon 23 (FIG. 4B). When the treatment balloon 23 is deflated, the elastic sleeve 48 exerts a circumferentially compressive force against the treatment balloon 23 radially inward toward the outer wall external surface 43 to cause a smooth, reduced cross-sectional (low) profile of the treatment balloon 23 along the axial extent of the treatment balloon 23. This smooth, reduced cross-sectional profile can facilitate passage of the catheter 40 through a body lumen during both insertion and extraction of the catheter 40. Preferably, the elastic sleeve 48 is sized and configured to snugly abut and circumferentially compress the treatment balloon 23 radially inward and tightly against the outer wall external surface 43 of the catheter 40.

In certain embodiments, the elastic sleeve 48 can be configured to facilitate the transfer of heat from the heated fluid (or other media) circulating within the treatment balloon 23. Preferably, the elastic sleeve 48 has a low thermal resistance such that a temperature drop through the elastic sleeve 48 is no greater than between about 0.5 degrees and about 1.5 degrees (0.5° C.–1.5° C.) relative to the temperature of the underlying surface of the device without such a sleeve. The elastic sleeve 48 is preferably formed from an elastomeric material having a Shore A (Type A) durometer range of between about 20 and about 60. As is known to those skilled in the art, a durometer is an international standard for the hardness measurement of rubber, plastic and other non-metallic materials. Durometers are described in the American Society for Testing and Material specification ASTM D2240.

Elastomeric materials from which the elastic sleeve 48 may be formed include, but are not limited to, silicone, natural rubber, synthetic rubber, and plasticized polyvinylchloride. Preferably, the thickness of the elastic sleeve 48 is between about 0.005 inches and about 0.030 inches (about 0.127–0.762 mm).

In certain embodiments, an upper portion 48u (FIG. 5) of the elastic sleeve 48 can be configured to surround and encase the anchoring balloon 22 and is secured to the tubular body 41. The upper portion of the elastic sleeve 48u (FIG. 5) may be attached to the tubular body 41 in various ways, as described above with respect to the elastic sleeve 48 that surrounds the treatment balloon 23.

The upper portion of the elastic sleeve 48u (FIG. 5) is adapted to inflate in response to inflation of the anchoring balloon 22 (FIG. 4C), and to deflate in response to deflation of the anchoring balloon 22 (FIG. 4B). When the anchoring balloon 22 is deflated, the corresponding or upper portion of the elastic sleeve 48u exerts a circumferentially compressive force against the anchoring balloon 22 radially inward toward the outer wall external surface 43 to cause a smooth, reduced cross-sectional profile of the anchoring balloon 22 along the axial extent of thereof. This smooth, reduced cross-sectional (low) profile can facilitate passage of (and reduce localized tissue irritation) the catheter as it moves through a body lumen into its desired operative position. Preferably, the elastic sleeve 48 is configured to circumferentially compress the anchoring balloon 22 radially inward and snugly/tightly against the outer wall external surface 43.

As such, anchoring balloons such as illustrated in FIG. 3, configured with non-smooth deflated configurations (i.e., wings 30) can have a smooth, reduced cross-sectional profile in a deflated condition via elastic sleeves according to embodiments of the present invention.

Elastic sleeves according to embodiments of the present invention can be utilized with treatment balloons (whether temperature or medicinal based therapeutic configurations), tissue-molding balloons (which can inhibit closure of passages or cause tissue to mold about the balloon or tubular stent as the tissue heals), and anchoring balloons having various shapes and configuration including, but not limited to, pear shapes, ramped or inclined shapes, bulbous shapes, elliptical shapes, oval shapes, cylindrical shapes, accordion pleated shapes, shapes with tapered fins, and the like.

The upper portion of the elastic sleeve 48u (FIG. 5) can be formed of the same or a different elastomeric material and/or material thickness than that of the remainder of the sleeve. In certain embodiments, the upper portion of the elastic sleeve 48u is preferably formed from the same material and as a unitary body with the remainder of the sleeve 48.

Figure 5:
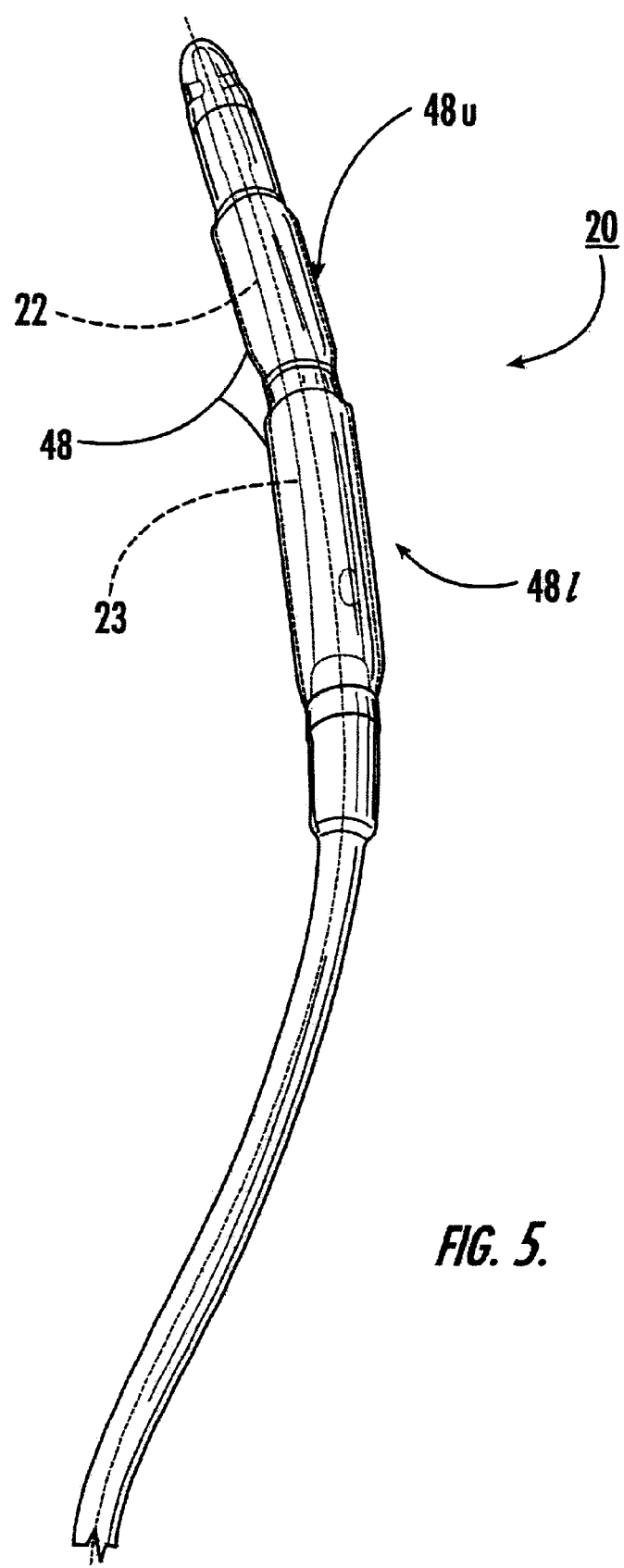
FIG. 5 is a perspective view of the thermal ablation treatment catheter of FIG. 3 according to embodiments of the present invention. This figure illustrates that the anchoring and treatment balloons are surrounded by a unitary elastic sleeve which imposes a low profile onto the underlying anchoring and treatment balloons when each are in respective deflated configurations.

In certain embodiments of the present invention, the elastic sleeve 48 is formed as a unitary body that surrounds both the anchoring and treatment balloons 22, 23. The sleeve 48 may also be formed as a single thickness or with varying thickness as desired. For example, a lesser thickness about the treatment balloon 23 may be used to promote heat transfer. As shown in FIG. 5, the upper 48u and lower 48l portions of the unitary sleeve 48 concurrently respond to the inflation and deflation of the respective underlying balloons.

FIG. 5 illustrates the thermal ablation treatment catheter 20 of FIG. 3 with the anchoring and treatment balloons 22, 23 encased and surrounded by a unitary elastic sleeve 48 which axially extends a proximate distance above and below the two balloons, 22, 23. In the illustrated configuration, the anchoring and treatment balloons 22, 23 are in respective deflated configurations and the unitary elastic sleeve 48 exerts a circumferentially compressive force against the anchoring and treatment balloons 22, 23 to cause the catheter 20 to have a smooth, reduced cross-sectional profile. Each of the sleeve regions corresponding to the underlying balloons may be independently expanded and collapsed (depending on the configuration/operation of the underlying inflatable segments).

Figure 6:
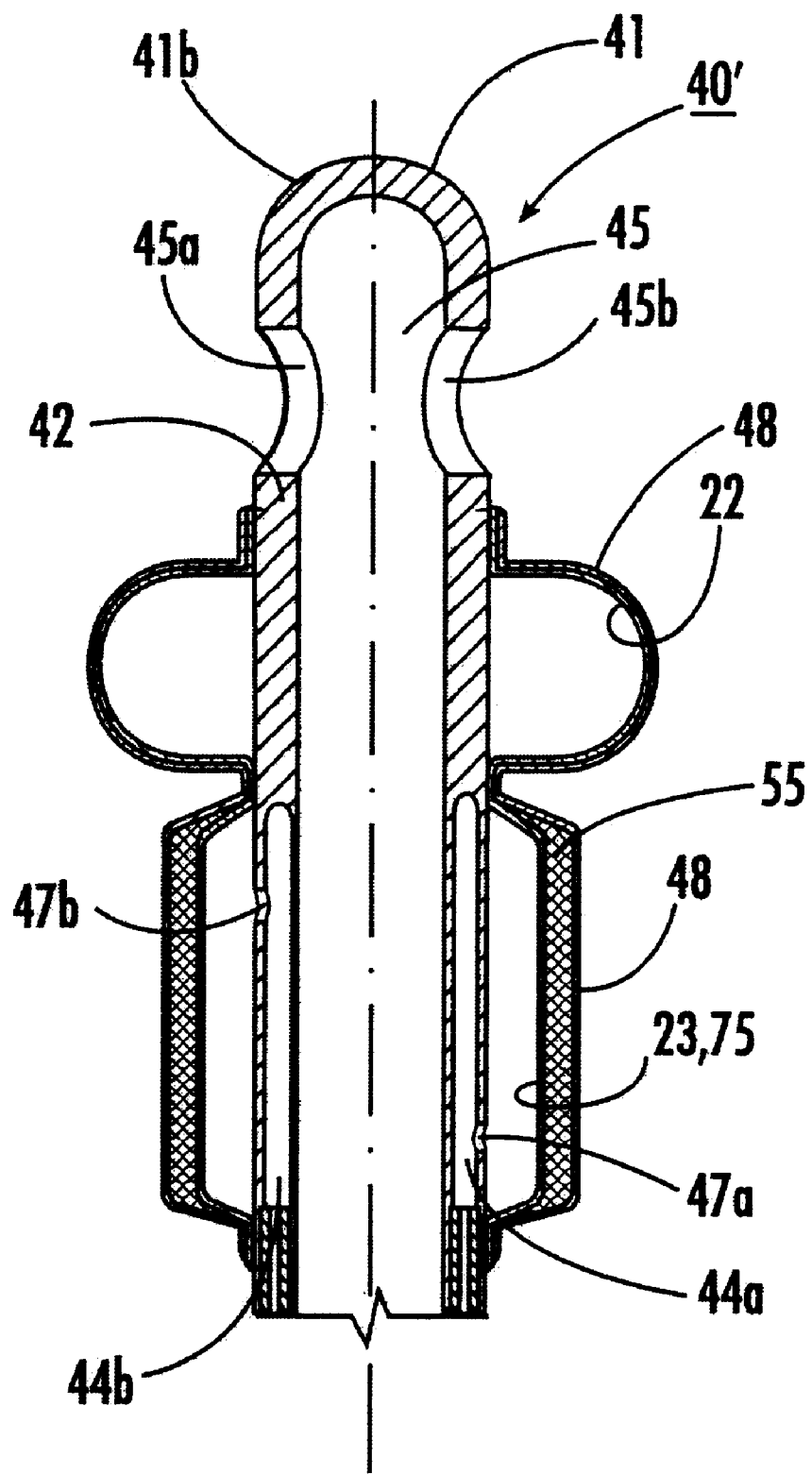
FIG. 6 is a side cutaway view of a medical device (i.e., a stent or catheter) according to another embodiment of the present invention, wherein a thin layer of fluid is disposed between at least one of the balloons and the elastic sleeve surrounding the balloon.

Referring now to FIG. 6, a medical device 40' (e.g., a catheter, stent) according to other embodiments of the present invention is illustrated. As shown, the medical device 40' includes a thin layer of biocompatible material and/or fluid 55 disposed between at least one inflatable segment 23, 75 and the elastic sleeve 48. The inflatable segment can be adapted to act as a treatment balloon 23 such as to deliver thermal and/or drug treatments to a targeted region and/or to act as a tissue molding balloon 75. The inflation paths and operation of the inflatable segments (anchoring balloon and lower inflatable segment) can be configured similar to that discussed for the embodiments shown in FIGS. 4–4D above.

In certain embodiments, the amount of fluid 55 disposed between the sleeve 48 and the underlying balloon 23, 75 can be sufficient to generate a layer thickness on the order of about 1.5 mm–1 mm or less. The fluid 55 and/or biocompatible material can be selected to facilitate heat transfer from the treatment balloon 23 to the subject through the elastic sleeve 48.

The biocompatible material or fluid 55 can be one or a combination of viscous or semi-viscous materials, creams or gelatinous materials (as will be discussed further below). The biocompatible material or fluid can also comprise oil (such as mineral or cooking oils like canola or olive oil), saline, or hydrogels. In certain embodiments, the fluid 55 comprises materials which transform physical states when exposed to treatment temperatures. For example, solid or semi-solid thin films which transform into a fluid state, viscous films which transform to solid particulate matter when exposed to the treatment temperatures, or materials which coagulate when exposed to certain temperatures, and the like.

In other embodiments, a solid or particulate matter can be combined with one or more of the fluids or materials described. The solid or particulate matter can be selected for its ability to absorb or accumulate and distribute the heat through the sleeve (such as ceramic microspheres or salt crystals or the like).

The material or fluid 55 is preferably selected to be non-toxic and to reduce potential noxious effects to the subject should a situation arise where the integrity of the treatment balloon 23 and/or the elastic sleeve 48 may be compromised, accidentally rupture, leak, or otherwise become impaired during service.

In some embodiments, the sleeve 48 can be configured to be permeable or porous and the fluid 55 can be configured to be released therethrough (such as in a liquid, fluid, or tissue-absorptive form) of a selected therapeutic treatment, medicament or drug which can be activated or released into the body through the sleeve over a period of treatment while the device 40 resides in the body.

In certain embodiments, the sleeve 48 with the underlying material 55 are held captured over the treatment balloon 23 and are configured to substantially retain the outer surface temperature of the treatment balloon compared to correspondingly configured sleeveless versions (temperature losses of no more than 0.5–2.0 degrees, and preferably no more than about 0.5–1.0 degrees). In other embodiments, the sleeve 48 and fluid 55 act in concert or together during thermal operation, to increase or enhance the temperature measured at the outer surface of the sleeve 48 over the temperature of the outer surface of the underlying surface of the sleeveless treatment balloon 23. For example, a sleeve 48 with a thickness of about 0.005–0.030 inches, and preferably about 0.020 inches (0.5 mm), can be disposed over the treatment balloon 23. A material 55 selected for its ability to substantially retain and/or increase the temperature of the outer surface (relative to the underlying surface measured without a sleeve) can be inserted therebetween.

Examples of suitable materials include, but are not limited to, biocompatible gelatinous, cream, or viscous or semi-viscous materials (under ambient conditions) such as petroleum jelly and other suitable biocompatible lubricants such as KY® jelly (or mixtures or derivatives thereof), and medications, anesthetics, or viscous creams such as LIDOCAINE or hydrocortisone cream. One suitable cream is a medicinal antibiotic and/or steroidal cream. The medicament can be selected for its ability to therapeutically treat urinary tract disorders, inflammation, diseases, or infections or to promote healing of the tissue thereat. An example of a steroidal cream which provides thermal enhancement and therapeutic treatment is believed to be FARCO-TRIL® cream available from Farco-Pharma, GmbH, 50829 Koln, Germany. This material is believed to contain (in one gram of viscous mixture) about 5.5% dioxyteracyclin, 1.27% polymyxin-B-sulfat, 10% hydrocortisone, and calcium. Other suitable steroid creams may include incipients that are sensitive to temperature, flaking or coagulating when exposed to treatment temperatures. Other medicines or materials, which may be suitable for use as a thermal enhancing, and/or treatment, of sleeve fluid 55, include certain of the coating materials hereinbelow.

In certain embodiments, the fluid 55 can be formulated such that it transforms into a thin solid or particulate film, which can evaporate during operation leaving a solid matrix with a viscous component in the sleeve 48.

The material 55 can be selected or formulated so that it is able to sustain a desired performance or functional viability or efficacy, or physical form, at use, even when exposed to sterilization processes such as ETO (ethylene oxide) or radiation exposure and the like used to sterilize the catheter or stent prior to use.

In certain embodiments, the material can be inserted into the sleeve and the assembly sterilized and sealed in sterile packaging, and the material is able to maintain the desired performance or functional viability or efficacy, or physical form, for a desired shelf life after sterilization and for a desired length of time in sterile packaging. Thus, in some embodiments, the catheter with the sleeve 48 and material 55 (which as noted above, can be a temperature enhancing material) may be labeled with a shelf-life or use date to assure the product has suitable or active viable fluids or materials 55 at its time of use. The sleeved catheter may seep during storage or sterilization and can be placed in a sealed sterile package to maintain sterility prior to use. The excess or seeped fluid which may exit the sleeve 48 so as to reside on the perimeter of the device 40 (or in the package proximate thereto) may provide lubrication upon insertion.

Configuring the fluid 55 as creams and gelatinous or viscous or semi-viscous materials may also allow ease of manufacture as these types of materials are less likely to flow out of position (they are retained upon the desired surfaces) as they are layered on the outer surface of the treatment balloon during assembly.

As the medical devices 40 of the present invention, including catheters or stents, can reside in the body for typically between 12–72 hours and potentially even longer (i.e., for post-treatment stents, about 2–14 days or even on a longer, more chronic basis), surface or other treatments or coatings may also be applied to, or integrated into or onto, the outer body of the device 40 to achieve one or more of increased lubricity, low coefficient of friction (each for easier insertion) as well as increased tissue biocompatibility, such as resistance to microbial growth and/or configured to reduce the incidence of urinary tract infection ("UTI") and/or to promote healing and/or inhibit scarring.

In addition or alternatively, the fluid 55 can be selected to travel out of the (permeable or semi-permeable) sleeve 48 over time while the medical device 40 (including the alternately configured devices such as those with the same numerical identifier in the figures herein) is positioned in the body.

In certain embodiments, the medical device 40 such as a catheter or stent, comprises a biocompatible protective coating which may include an anti-microbial or biostatic material, at least on its exposed surfaces (those that contact the body and/or the exposed surfaces of one or more of the inner fluid lumens). The biocompatible coating can inhibit the growth of undesirable microbial organisms such as bacteria, yeast, mold, and fungus while the catheter (shown as element 20 in FIG. 5) or stent (shown as element 70*a–f* in FIGS. 7A–7C, 8A–8B, 9A–9B) is held in the body. The protective coating can be provided by adding a conformal coating onto the desired shaft material such as a coating process which exposes the desired catheter surfaces to a gas-phase manomer of Parylene at low pressure (this type of coating process can be particularly suitable for silicone), such as is available from Parylene Coating Services, Inc. located in Katy, Tex.

The biocompatible biostatic or antimicrobial material can be chemically bound to the catheter or stent body such that it has a substantially non-leachable formulation or as a controlled time release agent so as to inhibit the formation of biofilms on the catheter and to inhibit or reduce infections caused by leaving the catheter or stent in the body for an extended period. The biocompatible coating can also be configured with anti-thrombogenic or anti-restenosis agents within the coating itself so as to generate a timed or slow release of same.

One suitable material may be the antimicrobial silver zeolite-based product available from HealthShield Technologies LLC of Wakefield, Mass. Another alternative is a Photolink® Infection Resistance antimicrobial coating or a hemocompatible coating from SurModics, Inc. of Eden Prairie, Minn. The coating may also include other bioactive ingredients (with or without the antimicrobial coating), such as antibiotics, and the like, as will be discussed further below.

In other embodiments, fluids can be delivered locally, such as through the inner lumen of the catheter 20 or stent 70 to the treated region. These fluids can be a number of different types and can be used to cleanse, deliver medicines to treat infections, promote healing, reduce scarring and the like. For example, fluids can be directed through the catheter drainage channel 45 and out into the body of the subject to cleanse the treated region after (and/or before or during) treatment to reduce the pathogen agents from the urinary tract and promote healing. For example, chlorhexidine gluconate (commercially known as HIBICLENS), povidone iodine (BETADINE), and sodium hypochlorite (CLOROX) can be delivered locally through the catheter positioned in the body of the subject. In addition, or alternatively, proteolytic enzymes (such as TRAVASE available from Boats Pharmaceuticals in Lincolnshire, Ill.) can be directed to the treated region, which may help digest necrotic soft tissue, which, in turn, may also help reduce the healing period and/or promote healing.

In other embodiments, fluids can be delivered locally to inhibit scar formation and/or to promote healing during the post treatment period. One such product that may be suitable for wound healing (including wounds caused by burns) is a hydrogel solution, is available from FibroGen, Inc., located in South San Francisco, Calif. Another hydrogel substance is extracted from the Aloe Vera L. plant. One commercially available product is identified as ULTREX, produced by Carrington Laboratories located in Irving, Tex. The woundhealing product can moisturize the treated region and inhibit infection as well as promote faster healing rates. These substances can be delivered immediately subsequent to the thermal treatment and/or at various times over the healing period. The substances may also be incorporated onto desired surfaces (or as the fluid in the sleeve 48) of the catheter or stent for automatic release of the substances in situ.

Various prophylactic antibiotics can also be delivered systemically such as orally, before and/or after a thermal treatment or thermal ablation session. In other embodiments, antibiotics or anti-inflammatory (including non-steroidal and α-blockers, Cox-inhibitors, or antioxidants) or other selected drugs, can be delivered directly into the treatment region. For treatment regions which are in locations which expose them to body contaminants such as the prostate, this can result in reduced catheterization time and reduced incidence of urinary tract infections (UTI). Antibiotics known as RIFAMPIN, MINOCYCLINE, MACROLIDES and VANCOMYCIN or others have been successfully used in certain medical or clinical sites. CELEBREX has also been used in conjunction with WIT of the prostatic urethra (given before and/or after the thermal ablation treatment). Nitrofuration (trade name MACRODANTIN) has been incorporated into the catheter itself to treat UTI and to promote faster healing. Alpha-blockers such as FLOMAX, CARDURA, and HYTRIN have also been used, as well as other agents such as DETROL, DITROPAN XL, and PYRIDIUM.

Examples of other anti-inflammatory medicines which may be used either locally and/or systemically with thermal treatments and thermal ablation therapies include, but are not limited to, steroids, nonsteroidal anti-inflammatory drugs such as tolmetin (trade name TOLECTIN), meclofenamate (trade name LEFLUNOMIDE), meclofenamate (trade name MECLOMEN), mefenamic acid (trade name PONSTEL), diclofenac (trade name VOLTAREN), diclofenac potassium (trade name CATAFLAM), nabumetone (trade name RELAFEN), diflunisal (trade name DOLOBID), fenoprofen (trade name NALFON), etodolac (trade name LODINE), ketorolac (trade name TORADOL) and other anti-inflammatory drugs such as leflunomide, rofecoxib (trade name VIOXX), ibuprofin (such as MOTRIN) and celecoxib (trade name CELEBREX). Other types of medicines or drugs can also be used such as anti-hypertensive drugs including terazosin (trade name HYTRIN), doxazosin (trade name CARDURA), and immunosuppressive drugs including cyclosporine (trade name SANDIMMUNE or NEORAL).

Additional examples of antibiotics that may be suitable for use in conjunction with thermal treatments including thermal ablations, include, but are not limited to, CIPRO, LEVAQUIN, SEPTRA, gentamycin, clindamycin (trade name CLEOCIN), azithromycin (trade name ZITHROMAX), trimethoprim (trade name TRIMPEX or PROLOPRIM), norfloxacin (trade name NOROXIN).

Angiogenesis inhibitors including for example, platelet factor-4, angiostatin, endostatin, and vasostatin, may also be used to form a portion of the fluid 55 or delivered locally or systemically to inhibit new vessel formation in connection with the delivered thermal therapy.

In addition, or alternatively, the catheter 20 or stent 70 may be configured with a biocompatible lubricant or low-friction coating material (at least along selected regions so as not to interfere with the heat transmissivity at the treatment balloon) to help reduce any discomfort associated with the insertion of the device into the body. Coatings, which may be appropriate, include coatings that promote lubricity and wettability. The coatings may be provided such that the hydrophilic state is transient or more permanent. Conventional processes such as plasma, corona, or ozone processing are thought to have a transient hydrophilic state. In contrast, a stable long term hydrophilic state may be provided by the use of HydroLAST™ from AST which proposes a submicron coating to alter a hydrophobic substrate into a long term or permanent hydrophilic substrate.

The hydrophilic coating can be applied as a thin layer (on the order of about 0.5–50 microns thick), which is chemically bonded with UV light over selected external surfaces of the catheter 20 or stent 70 (such as proximate the distal end and along the shaft). One such product is a hydrophilic polymer identified as Hydrolene® available from SurModics, Inc., of Eden Prairie, Minn. Other similar products are also available from the same source. Another suitable product may be HydroLAST™ from AST that proposes a submicron coating to alter a hydrophobic substrate into a long term or permanent hydrophilic substrate.

Still further, the catheter 20 or stent 70 may be configured to provide both the lubricious coating and bioactive ingredients which can be configured to provide sustained or time release matrices of antibiotics, antimicrobial, and anti-restenosis agents, identified as LubrilLast™ from AST as noted above. Another product which may be suitable are medical hydrogels such as identified by the name of Aquatrix™II, available from Hydromer, Inc. located in Branchburg, N.J. Examples of products which can provide one or more of microbial resistance, wet lubricity, biocompatibility, and drug delivery include coatings such as LubriLAST™, a lubricious coating, available from AST of Billerica, Mass., and coatings available from Hydromer Specialty Coatings (this company also provides a non-leaching radio-opaque polymeric coating). These coatings may be formulated as a matrix onto selected surfaces of the catheter body to provide a timed-release dispersion of the desired treatment (such as drug delivery) into the body (i.e., "biodegradable or bioabsorbable coatings").

In each of the embodiments described herein, the catheter or stent and coatings or fluids held therein are preferably configured to withstand suitable sterilization processes as they will be used in medical applications.

In certain embodiments, a quantity of small particulate matter can be added to the fluid 55 to enhance the heat conductivity in this region. For example, a quantity of ceramic microspheres can be used. The insulation mixture can comprise at least about 10% volume of ceramic microspheres. The ceramic or silica microspheres can be hollow and sized in the range of about 106–350 µm. In certain embodiments, the mixture is formulated to have a volumetric ratio of between about 2:1–15:1, and preferably a ratio of between about 3:1–5:1, volume of liquid to microspheres. Other miniaturized (miniaturized typically meaning sized in the range of about 10–750 µm) preferably, hollow, bodies can also be used according to the present invention. The ceramic or silica microspheres can be integrated into the wall material of the sleeve 48 or combined with the fluid. Ceramic hollow microspheres sized with average ranges of about 106 and 350 µm are available from CHL Microspheres, Inc., located in Helenwood, Tenn. For more discussion of ceramic particulates, see co-pending and co-assigned U.S. patent application Ser. No. 10/011,700, the contents of which are hereby incorporated by reference in its entirety herein.

As noted above, particularly when used with catheters formed to deliver thermal therapies, the fluid 55 and the elastic sleeve 48 can be configured to have a combined low thermal resistance such that a temperature drop through the fluid 55 and the elastic sleeve 48 is no greater than between about 0.5 degrees and about 1.5 degrees (0.5°–1.5°). And, as discussed above, in certain embodiments, the sleeve 48 and fluid 55 are selected to increase the temperature at the outer surface compared to the temperature without such a sleeve (no temperature loss) due to the accumulation or localized capture and retention of energy/heat in the substance or liquid 55 under the sleeve 48.

Examples of catheters that can be configured according to embodiments of the present invention include those described in U.S. Pat. Nos. 5,916,195 and 5,257,977, and in U.S. patent application Ser. No. 09/239,312, filed Jan. 29, 1999, which are incorporated herein by reference in their entirety. However, it is understood that catheters of various configurations and sizes may incorporate elastic sleeves according to embodiments of the present invention.

As is known to those of skill in the art, a stent is a medical device used to hold open a body lumen (e.g., artery, urethra, etc.) that is obstructed or has recently been cleared or opened via some medical procedure, such as an ablation technique, which has a tendency to close or restrict the passage due to post-treatment inflammation. Examples of stents that can be configured according to embodiments of the present invention are described in detail in U.S. patent application Ser. No. 60/215,156, filed Jun. 30, 2000, and its corresponding U.S. application Ser. No. 09/837,486, the disclosures of these applications are hereby incorporated herein by reference as if recited herein in their entirety.

Turning again to FIG. 6, it is noted that, in certain embodiments, the anchoring balloon 22 can be configured to radially expand a greater radial distance (and in some embodiments a substantially greater distance such as 2× or greater) than the more distal treatment or tissue-molding balloon 23, 75, respectively.

It is noted that the term "treatment balloons" are intended to include those balloons or inflatable segments that radially expand to deliver thermal or drug therapies to local tissue. The term "tissue molding balloons" are intended to include those balloons or inflatable segments which expand to cause the tissue threat to form about the perimeter of the stent body and thus restrict the closure in a localized region of a natural body lumen or cavity. Some medical devices 40 may configure the treatment balloon to also act as a tissue molding balloon or to have both a tissue molding balloon which is independently inflatable underlying or overlying the treatment balloon. FIG. 6 illustrates that the elongated inflatable segment may be either or both a tissue molding balloon 75 or a treatment balloon 23, depending on the operative configuration or desired application.

Referring now to FIGS. 7A–7C, 8A, 8B, 9A and 9B, the medical device 40" shown are stents 70a–f, which are configured for insertion into a body lumen according to embodiments of the present invention. In certain embodiments, heat transfer characteristics of the sleeve 48 or material 55 may not be as great of a concern, particularly where the stent may be used post-treatment to mold the opening size of the treated tissue such as during a portion of the healing process. As noted above, the material 55 may be formulated as a viscous or semi-viscous or fluid substance and/or formulated to provide one or more bioactive therapeutic substances.

Figure 7A:
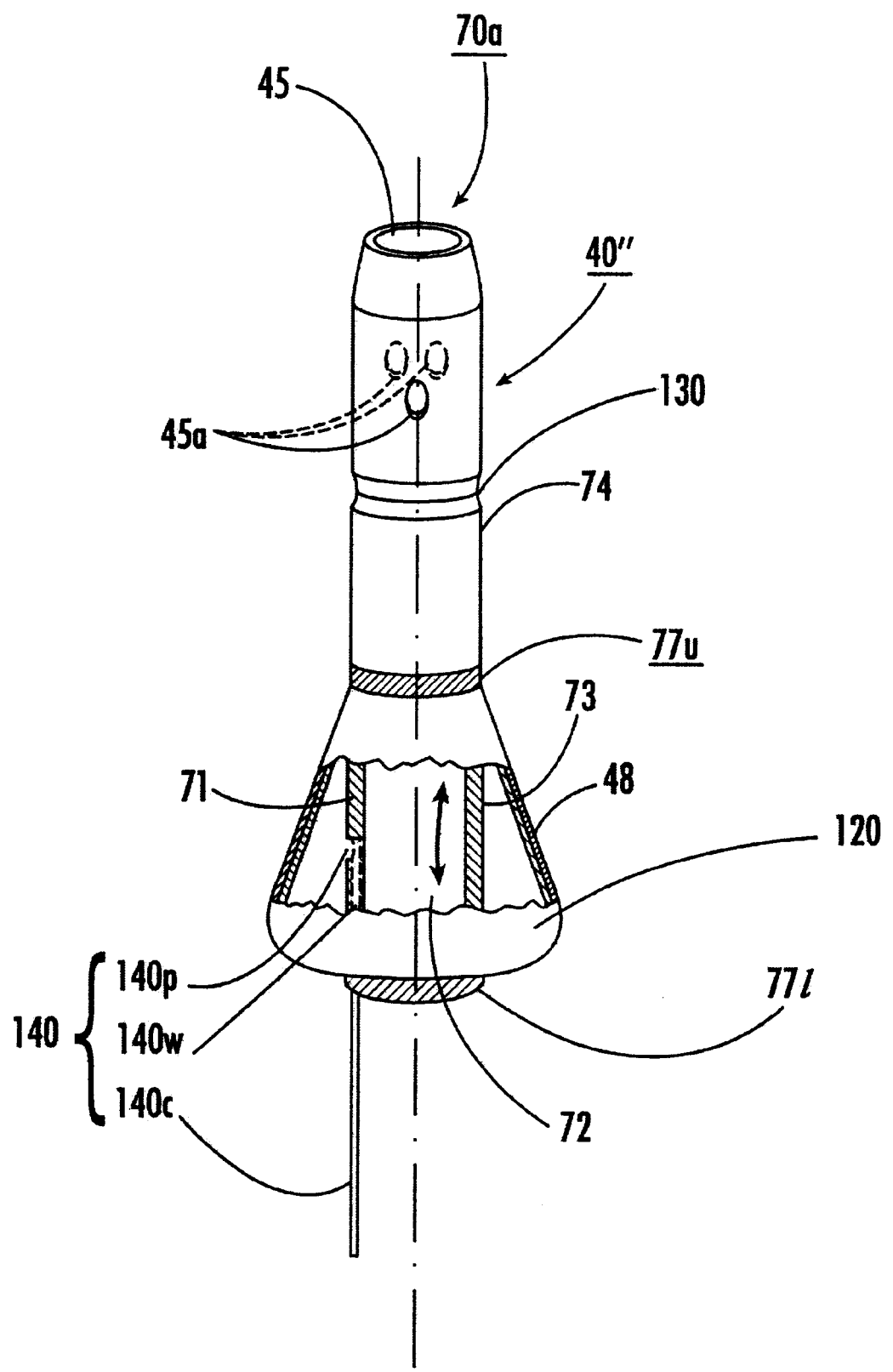
FIG. 7A is a front partial cutaway view of a stent with a sleeve disposed over a lower localized tissue-anchoring balloon according to embodiments of the present invention.

Referring first to FIG. 7A, the illustrated stent 70a includes a unitary tubular body 71 having an axial bore 72 and an outer wall 73 with an external surface 74. The stent 70a shown includes a peripherally mounted fixation or tissue-anchoring balloon 120 which is configured to expand to help hold the stent 70a in a desired position in the body. The sleeve 48 is disposed over the tissue-anchoring balloon 120. As shown, the axial bore 72 defines the drainage lumen 45 (and/or drug delivery channel). The stent 70a can include circumferentially extending radiopaque strips 77u, 77l. As shown, the unitary stent body can include at least one increased resilience segment 130 to allow the unitary body to expand or retract axially as the physiology of the body changes to exert tension or compressive forces thereon. An inflation path 140 extending between an inflation source (not shown) via a conduit 140c and a passage in the wall 140w to a port 140p in fluid communication with the tissue-anchoring balloon 120 is used to inflate and deflate same.

Suitable media for causing the fixation or tissue-anchoring balloon 120 to inflate (similar to the other inflatable segments) includes gases, liquids, or solids/powders or mixtures thereof, including, but not limited to, air, noble gases such as nitrogen and helium, oxygen, water, and oils (such as canola oil, olive oil, and the like). Preferably, such media is selected to be non-toxic and to reduce any noxious effect to the subject should the integrity be compromised, accidentally rupture, leak, or otherwise become impaired.

Figure 7B:
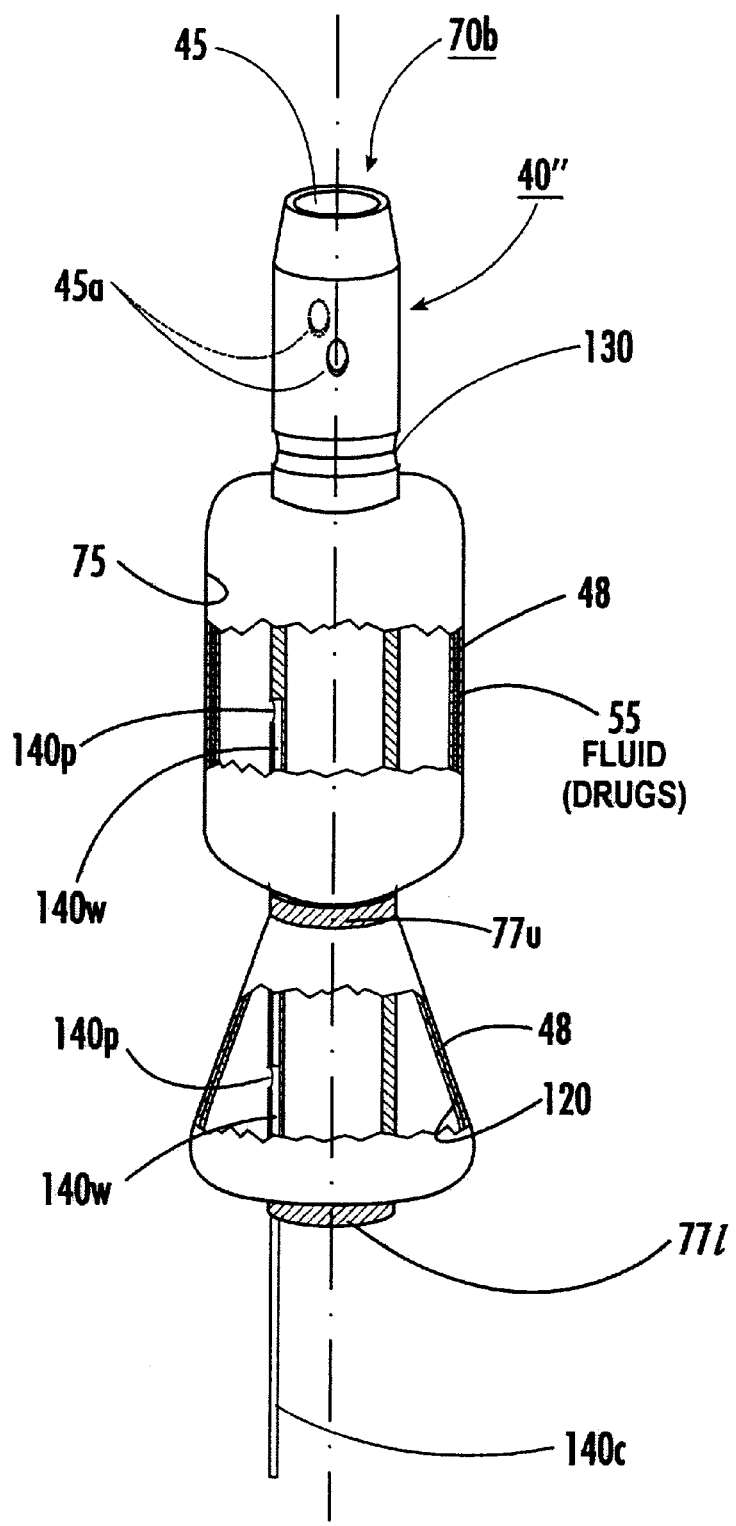
FIG. 7B is a front partial cutaway view of a stent with at least one sleeve disposed over a tissue molding and localized anchoring balloon according to embodiments of the present invention.

FIG. 7B illustrates a stent 70b similar to that shown in FIG. 7A, but with two inflatable segments, both a lower fixation or tissue anchoring balloon 120 and a tissue-molding balloon 75 thereon. As shown, the two inflatable segments 75, 120 may be in fluid communication and concurrently inflatable. In the embodiment shown, the wall passage 140w extends up a further distance to another (upper) port 140p. The upper port 140p is in fluid communication with the tissue-molding balloon 75 and the inflation source (and the lower port 140p at the lower balloon 120). Alternatively, a separate conduit and wall channel (not shown) can be used to inflate the tissue-molding balloon 75 (the tissue-molding balloon may also act as a treatment balloon 23 as noted hereinabove).

Figure 7C:
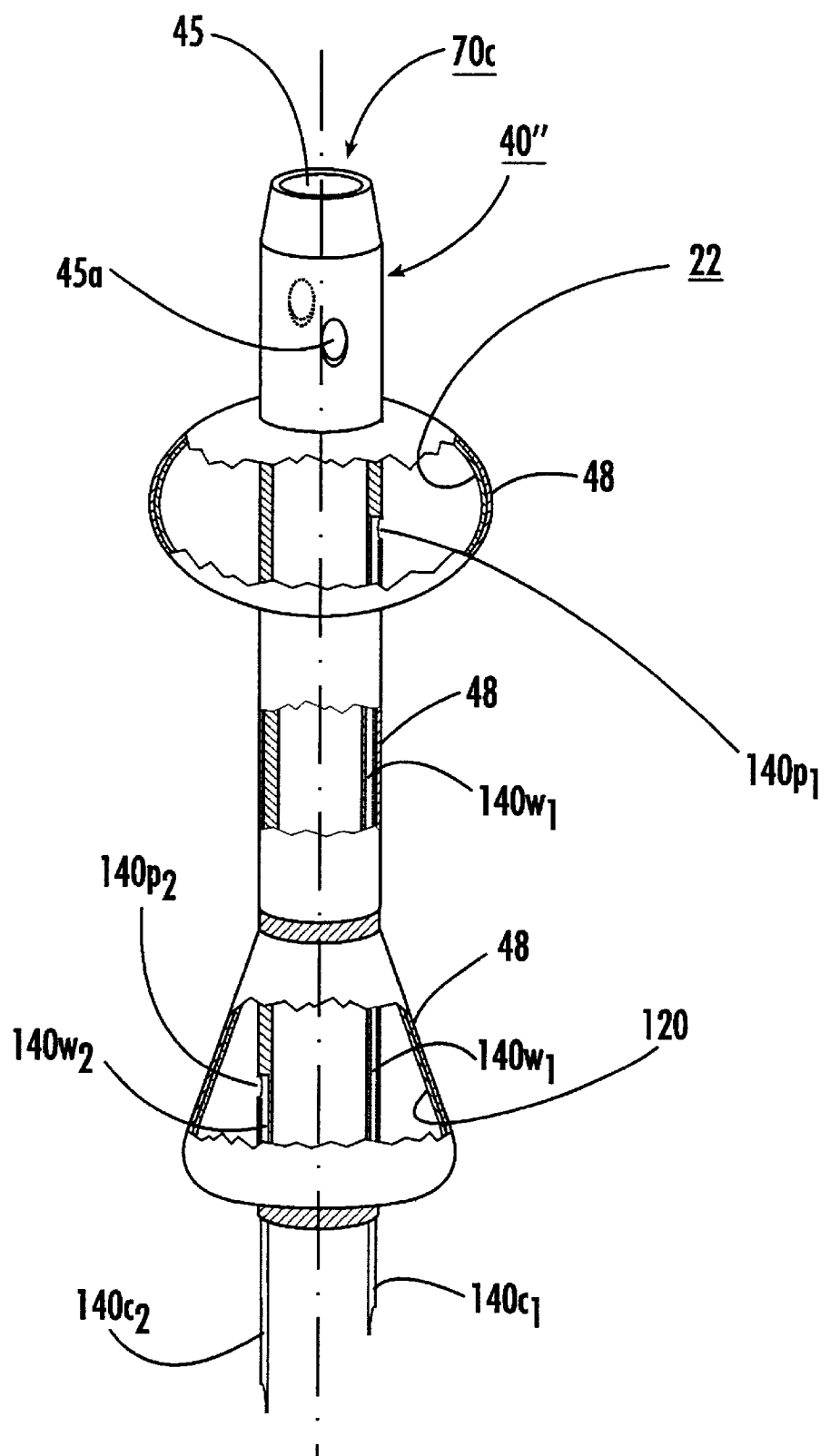
FIG. 7C is a front partial cutaway view of a stent with at least one sleeve disposed over the bladder anchoring balloon and the localized anchoring balloon according to embodiments of the present invention.

FIG. 7C illustrates a stent 70c which includes an upper anchoring balloon 22 covered with an upper portion of the sleeve 48 and a lower fixation or tissue-anchoring balloon 120 covered with a lower (or central) portion of the sleeve 48. Each outwardly inflatable balloon 22, 120 has a respective inflation conduit, wall channel, and wall port, 140c1, 140w1, 140p1 and 140c2, 140w2, 140p2.

Figure 8A:
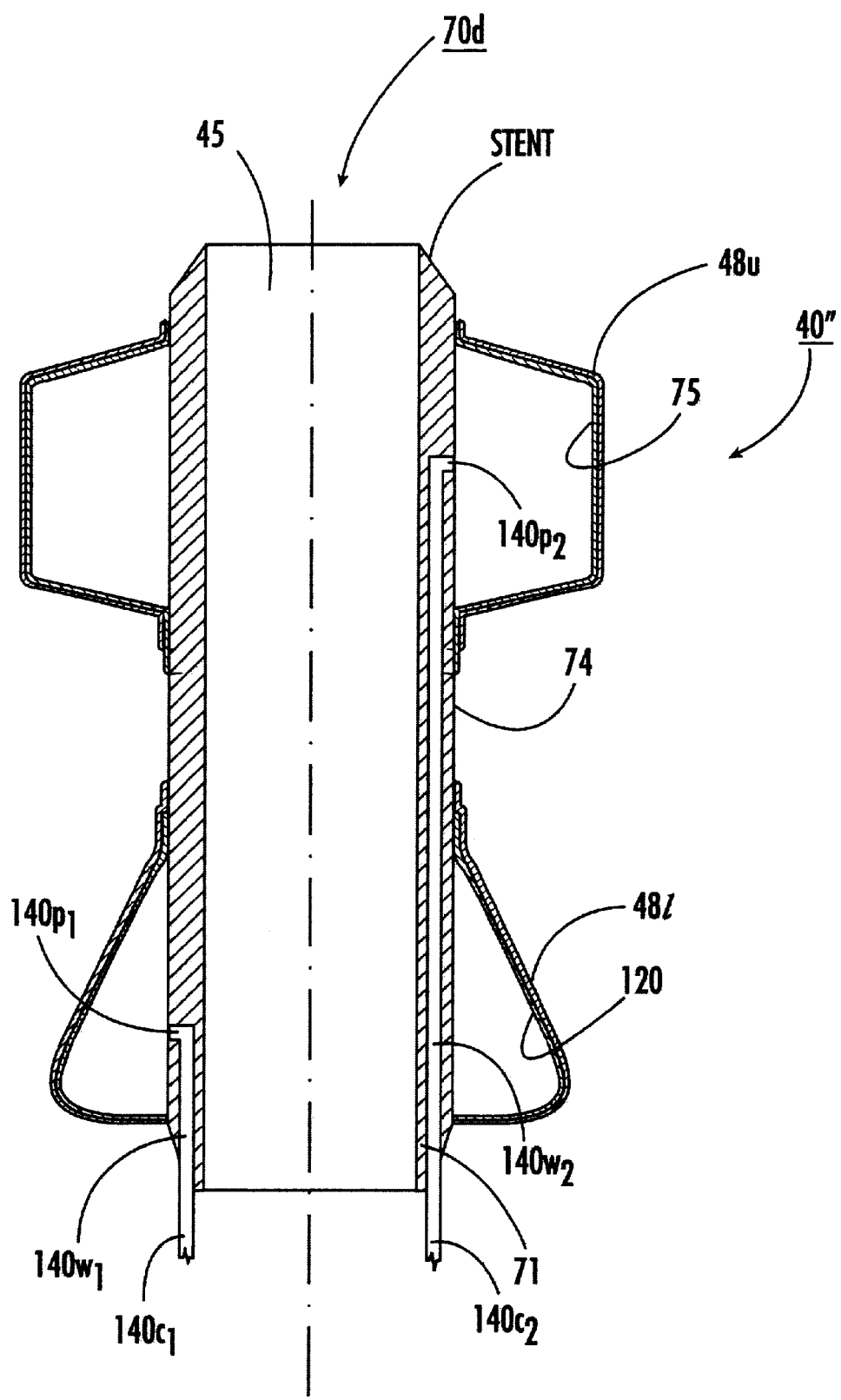
FIG. 8A is a side cutaway view of a stent having a tissue molding balloon and localized anchoring balloon. As shown, each balloon is surrounded by an elastic sleeve, and the tissue molding and anchoring balloons are in an inflated condition.
Figure 8B:
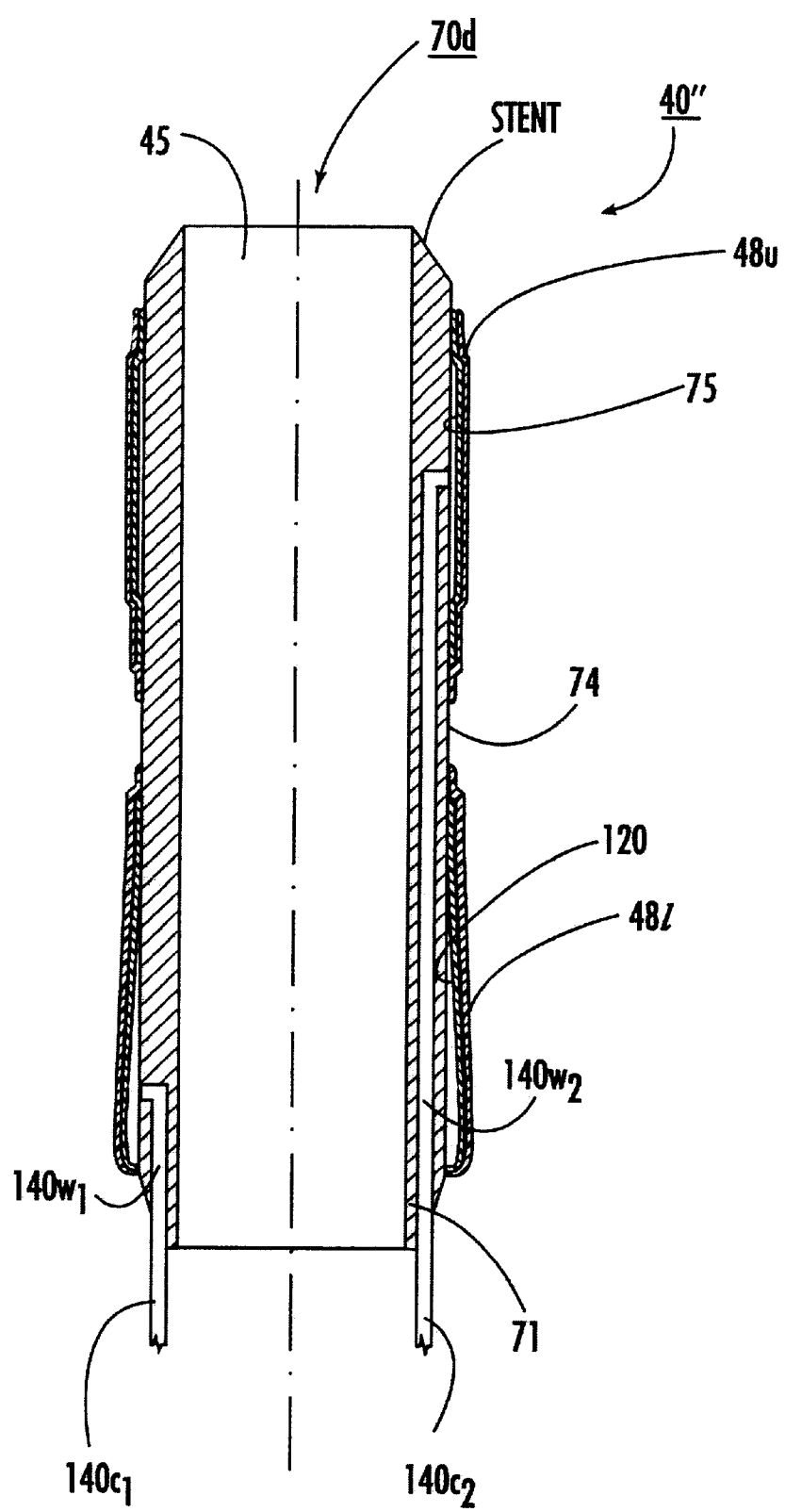
FIG. 8B is a side cutaway view of the stent of FIG. 8A with the balloons in a deflated condition with the sleeve exerting a compressive force thereon such that the stent has a low, smooth profile.

FIG. 8A illustrates a stent 70d similar to the embodiment of FIG. 7B, but has an alternatively configured top end portion and employs two physically separate sleeves 48u, 48l, a respective one each over the tissue molding balloon 75 and the fixation or lower anchoring balloon 120. The stent 70d of FIG. 8A also includes two separate inflation paths (each in fluid isolation) such that the two inflatable segments are independently inflatable. FIG. 8B illustrates the stent 70d in a low profile deflated condition.

Figure 9A:
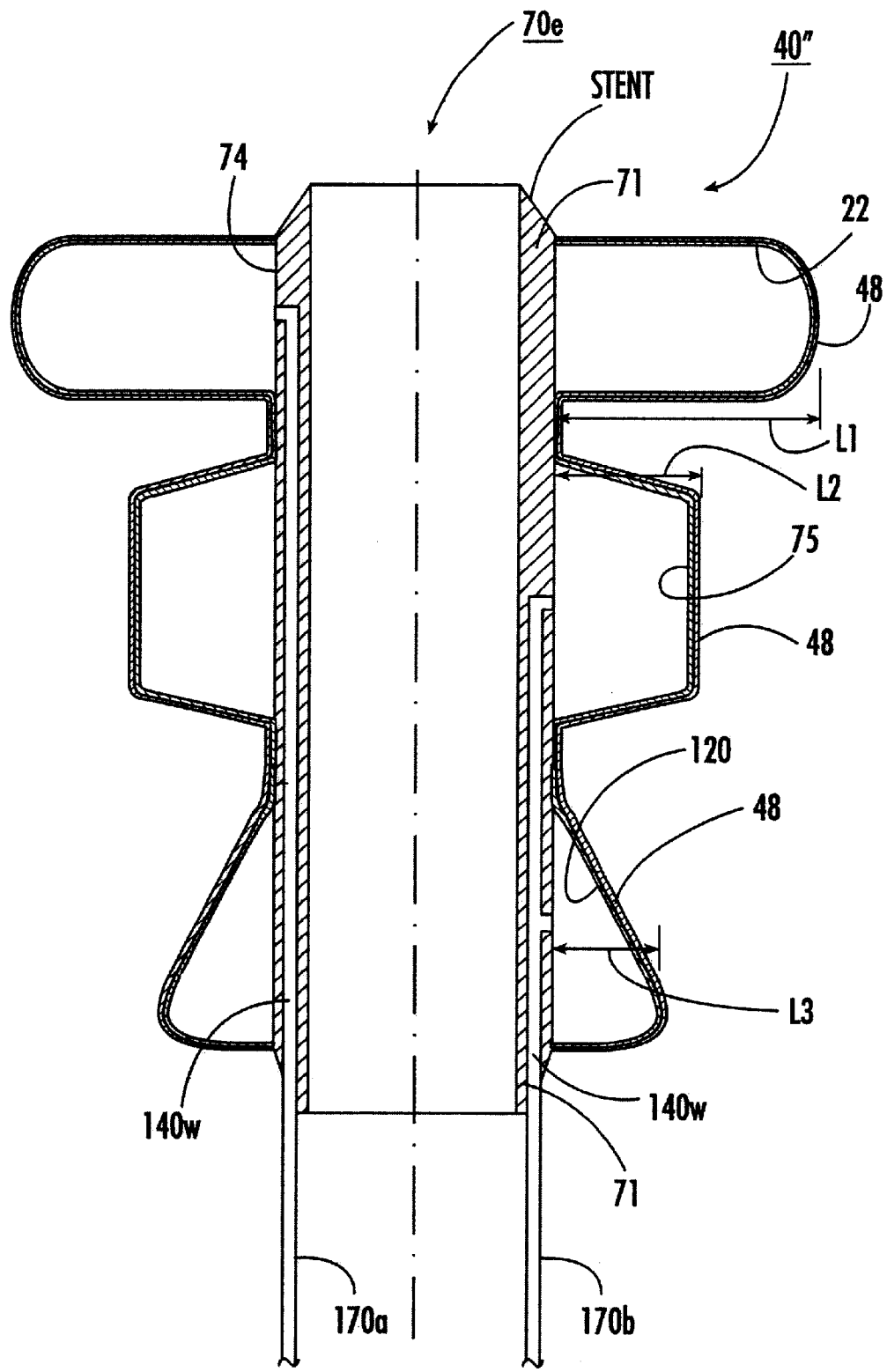
FIG. 9A is a side cutaway view of a stent that includes a bladder-anchoring balloon, a tissue-molding balloon, and a localized anchoring balloon (each in an inflated configuration) according to embodiments of the present invention. As shown, each balloon is surrounded by a respective elastic sleeve (or a unitary elastic sleeve extending along the perimeter of the body such that it overlies each of the three balloons) according to embodiments of the present invention.
Figure 9B:
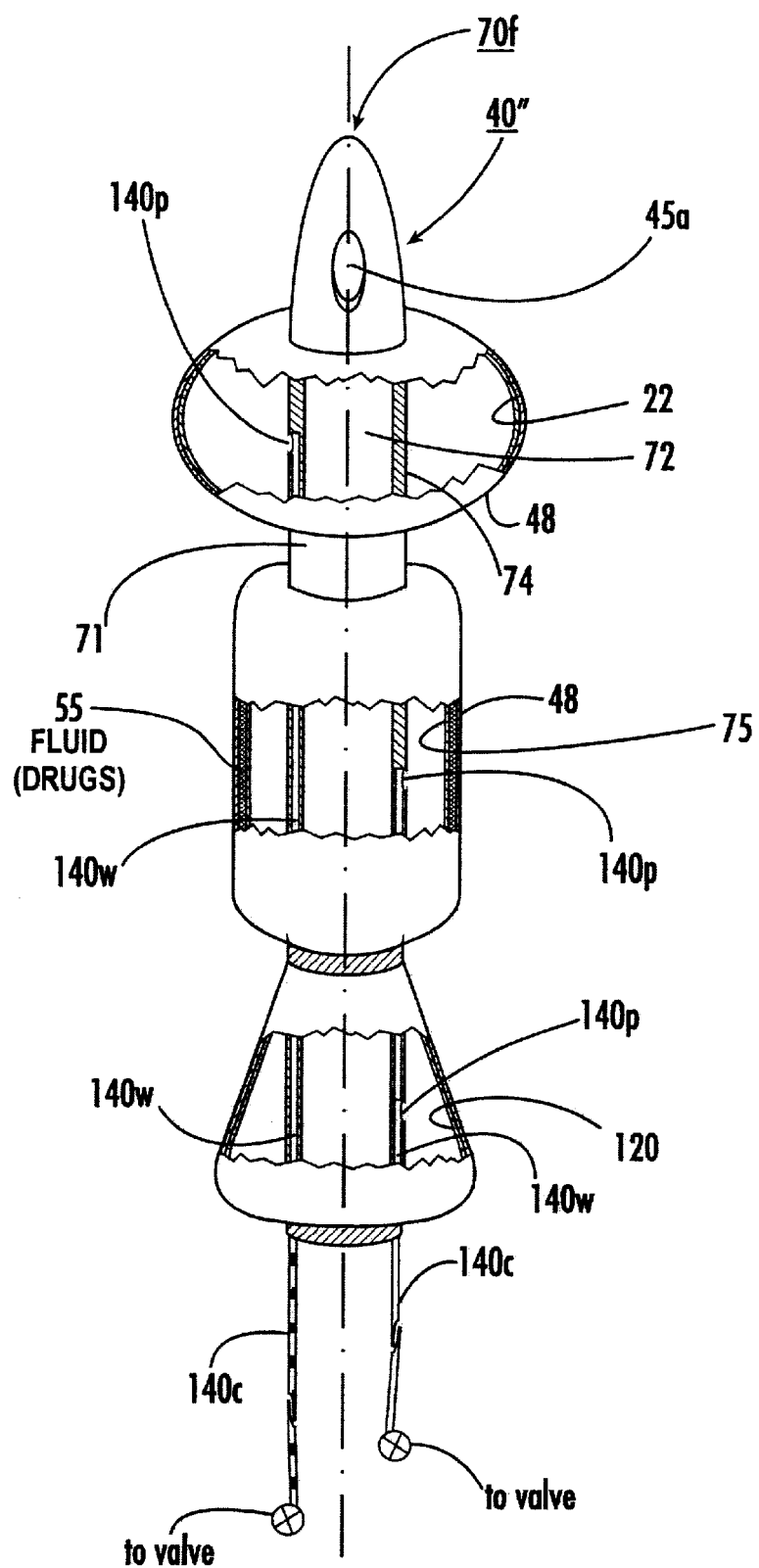
FIG. 9B is a front partial cutaway view of a medical device (catheter and/or stent) with a sleeve extending to encase three different inflatable segments similar to FIG. 9A. As shown, the upper portion of the body has a closed end according to embodiments of the present invention.

FIGS. 9A and 9B illustrate stents 70e and 70f, respectively, each having three inflatable segments thereon. As shown the three inflatable segments include in serial order from a distal to a more proximal position, a bladder anchoring balloon 22, a tissue-molding balloon 75, and a fixation or tissue anchoring balloon 120. FIG. 9A illustrates an open (distal) end configuration and FIG. 9B illustrates a closed end configuration.

In each of the stent or catheter or medical device embodiments, as described for catheters above, a desired material such as a fluid 55 (such as shown, for example, in FIG. 9B) may be disposed intermediate one or more of the inflatable segments and the overlying sleeve 48. As noted above, the fluid 55 may be chosen such that it is viscous or semi-viscous (such as a cream or gel-like material) at ambient temperatures such that it is resistant to flow off the wall of the device. The fluid 55 may be selected for its therapeutic or anesthetic properties, and in certain embodiments, the fluid may be formulated such that it is both a therapeutic and anesthetic for the subject as described above.

As noted above, the fluid 55 is preferably selected to be non-toxic and to reduce any potential noxious effect to the subject should a situation arise where the integrity of the elastic sleeve 48 may be compromised, accidentally rupture, leak, or otherwise become impaired during service.

As before, in operation, referring to FIG. 9A, the elastic sleeve 48 surrounds and snugly encases one or more of the balloon(s) such that each are concurrently responsive to the introduction of pressure thereto. As shown, the sleeve 48 encases the underlying tissue molding balloon 75 and can also be configured as a unitary body to extend down over the lower localized anchoring balloon 120 and up and over the bladder anchoring balloon 22. The elastic sleeve 48 can be a unitary body which is secured to the tubular body 71 and is configured to inflate locally in response to inflation of the underlying balloon, and to locally deflate in response to deflation of thereof. In this embodiment, a unitary sleeve 48 continuously extends over the perimeter surface of the stent from the top of the anchoring balloon 22 to the bottom of the fixation or tissue-anchoring balloon 120. Fluid 55 may be inserted therebetween one or more of the balloons and the sleeve 48 as desired (not shown).

Each of the balloons may be independently or separately inflatable. In certain embodiments, it may be preferred that at least the bladder-anchoring balloon 22 is separately inflatable from the others. As shown, the balloons may be configured and sized to expand to different radial distances, the upper anchoring balloon 22 radially expandable to the largest cross-sectional span or length "L1", the tissue molding balloon 75 to the second largest length "L2" and the fixation or localized tissue anchoring balloon 120 to the lesser length "L3". As such, the sleeve 48 is differentially expandable in three different cross-sectional widths corresponding to the underlying balloon 22, 75, 120. The "L1" length may be twice as great as the next lesser cross sectional span or length of the other balloons. The sleeve 48 can be reinforced or attached to the underlying tubular body 71 at each of the transition zones between the balloons or can extend free about the outer perimeter of the underlying body 71 and balloons 22, 75, 120, as desired.

As for embodiments discussed above, when the balloons are deflated, the elastic sleeve 48 exerts a circumferentially compressive force against the balloons radially inward toward the outer wall external surface 74 to cause the device to take on a smooth, reduced cross-sectional profile along an axial extent of the balloons (FIG. 8B). This smooth, reduced cross-sectional profile can facilitate passage of the stent 70a–f through a body lumen during both insertion and extraction of the stent 70.

As before, in certain embodiments, the elastic sleeve 48 for stents can be formed from an elastomeric material having a Shore A (Type A) durometer range of between about 20 and about 60. The thickness of the elastic sleeve 48 can be between about 0.005 inches and about 0.030 inches (about 0.127–0.762 mm).

Elastomeric materials from which the elastic sleeve 48 may be formed for embodiments of the stent applications include, but are not limited to, silicone, natural rubber, synthetic rubber, and plasticized polyvinylchloride (PVC), and in situ or in vivo biodegradable materials. For the biodegradable materials, the sleeve 48 (or a portion thereof) may be configured such that it is absorbed into the body over time. Examples of suitable biodegradable materials include polymers, copolymers and polymer compositions. Exemplary biocompatible biodegradable absorbable materials are described in U.S. Pat. Nos. 6,171,338; 4,743,257; 4,700,704; U.S. Pat. No. 4,655,497; U.S. Pat. No. 4,649,921; U.S. Pat. No. 4,559,945; U.S. Pat. No. 4,532,928; U.S. Pat. No. 4,605,730; U.S. Pat. No. 4,441,496; U.S. Pat. No. 4,435,590; and U.S. Pat. No. 4,559,945. The contents of these patents are hereby incorporated by reference as if recited in full herein.

As described above, the sleeve 48 and any underlying material 55 can be configured to be viable after exposure to sterilization processing with sufficient shelf life for efficacy at use.

In the illustrated embodiment of FIG. 8A, the localized tissue anchoring balloon 120 and corresponding elastic sleeve portion 48 have respective frustoconical shapes in the inflated configuration. However, it is understood that stents according to embodiments of the present invention can have anchoring balloons and corresponding elastic sleeves with various shapes and configuration including, but not limited to, pear shapes, ramped or inclined shapes, bulbous shapes, elliptical shapes, oval shapes, cylindrical shapes, accordion pleated shapes, shapes with tapered fins (such as circumferentially disposed about the perimeter of the lower portion of the stent body), and the like.

For a prostatic stent application, the stent may be configured to be minimally invasive to allow natural operation of the sphincter. The upper balloon 22 can engage with the bladder neck to lock the stent in location relative to the bladder while the molding balloon 75 can align with the prostatic urethra (in the treated area), and the fixation or tissue anchoring balloon 120 can align with the membraneous urethra above the sphincter (the membraneous urethra is located between the verumontanum and the sphincter). Small cross-sectional conduits or tubes 140c (substantially smaller than the width of the stent body), one or a plurality (shown as two), can be used to inflate the balloons. In the prostatic applications, the sleeve 48 is preferably configured to sustain sufficient elasticity after being in an expanded state for between 2–14 days to be able to circumferentically compress the underlying balloons to a low profile condition for removal from the subject. The stent may also include selected therapeutic and/or anesthetic materials 55 inserted into the sleeve, which may be viscous or semi-viscous as noted above.

In thermal treatment catheters, the sleeve 48 may be configured to provide sufficient compressive forces to cause the low profile configuration even after exposure to thermal treatment temperatures for 30–60 minutes. In certain embodiments, the sleeve 48 can be configured to retain sufficient elasticity after exposure to ablation level temperatures for at least 30–50 minutes.

In the figures, the sleeve 48 is shown in some embodiments as either a discrete or a unitary contiguous sleeve. The present invention contemplates both a unitary contiguous sleeve and a plurality of discrete elastic sleeves, depending on the application, which are configured to overlie one or more of the balloons.

The invention will now be illustrated with reference to certain examples which are included herein for the purposes of illustration only, and which are not intended to be limiting of the invention.

EXAMPLES

Several experiments were performed with two different thickness sleeves. FIGS. 10A, 10C, 11A, and 11C correspond to experiments using catheters with thinner walled treatment balloons than the remainder of the experiments. In addition, the temperature measurements were obtained for embodiments using the sleeve alone and with different fluid materials inserted in between the sleeve and the treatment balloon.

The incremental balloon surface measurement points shown in the graphs were taken at increments of 2 mm. Certain of the experiments obtained two sets of measurements at two different radial positions corresponding to the two "hottest" lines extending along the length of the cylindrical portion of the treatment balloon. Position 1 measurements were taken along a line at the outer surface of the treatment balloon or sleeve corresponding to where the "outlet" aperture of the circulating liquid was facing up (with the inlet port down at 180 degrees from the measurement points). Position 2 measurements were taken where the inlet aperture was facing up (under the measurement line). The measurements were taken ex vivo. The points on the graphs represent a mean value with a +/– standard deviation spread (5 measurements were obtained for each result).

The fluid was heated outside the body to a target temperature or setting of 60 degrees or 62 degrees Celsius and then circulated through the catheter into the treatment balloon. In most of the graph figures, the three different lines shown correspond to: (a) the temperature of the balloon surface without the use of a sleeve; (b) the temperature of the sleeve surface where the sleeve is over the treatment balloon; and (c) the percentage temperature drop (or increase) based at various corresponding points about the treatment balloon due to the presence of the sleeve (and/or other material) over the treatment balloon.

Figure 10A:
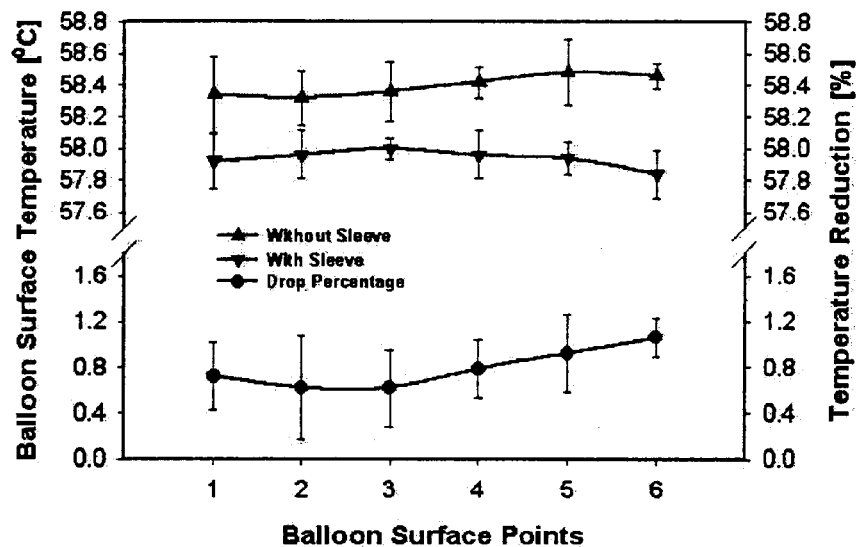
Figure 10B:
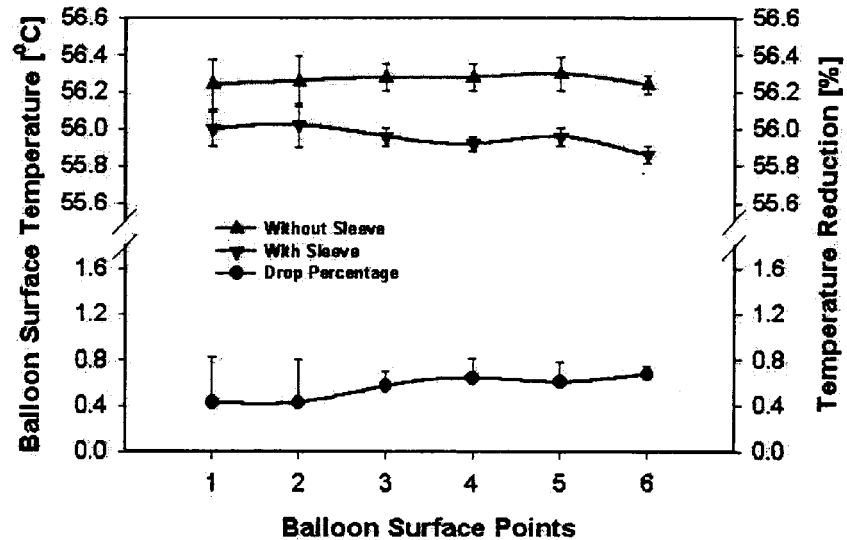
Figure 10C:
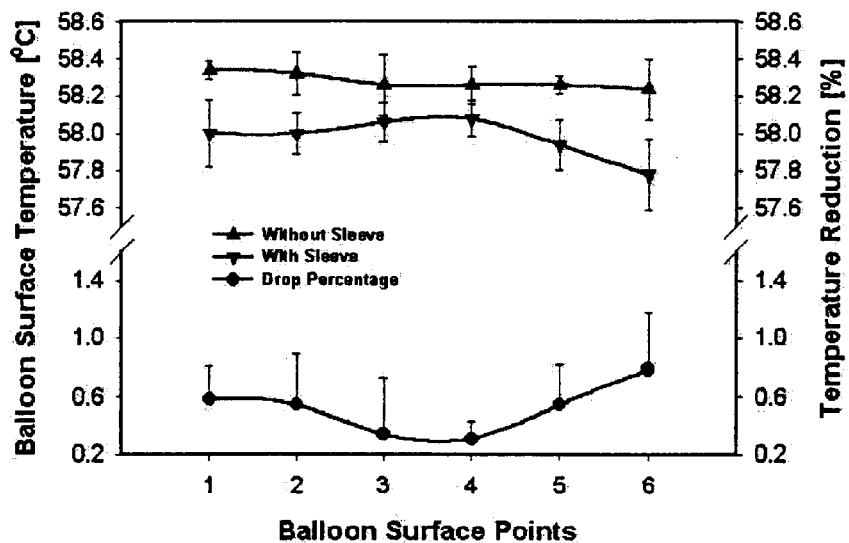

The results shown in FIGS. 10A and 10C were obtained during a first set of experiments using a sleeve having a thickness of 0.127 mm (0.005 inches) and a durometer of about 50 A which was overlaid on top of the treatment balloon 23 similar to the embodiment shown in FIG. 5. The sleeve was heat-treated (cured for four hours). The first set of experiments used a catheter with a thinner treatment balloon wall thickness than the experiments for FIG. 10B and the others. In operation, the heated fluid generated heat in the treatment balloon which then passed through an increased thickness (through the thickness of the treatment balloon and the thickness of the sleeve) over the heat transmission path compared to the heat transmission path provided by the use of a sleeveless treatment balloon.

In FIGS. 10A and 10C, during exposure to ablation level temperatures, the maximum ex vivo temperature drop attributed to the sleeve was for the 60 degree temperature setting (a) at position 1, about 0.6 degrees or below about a 1.1% decrease and (b) at position 2, about 0.5 degrees and less than a 0.9% decrease.

Figure 11A:
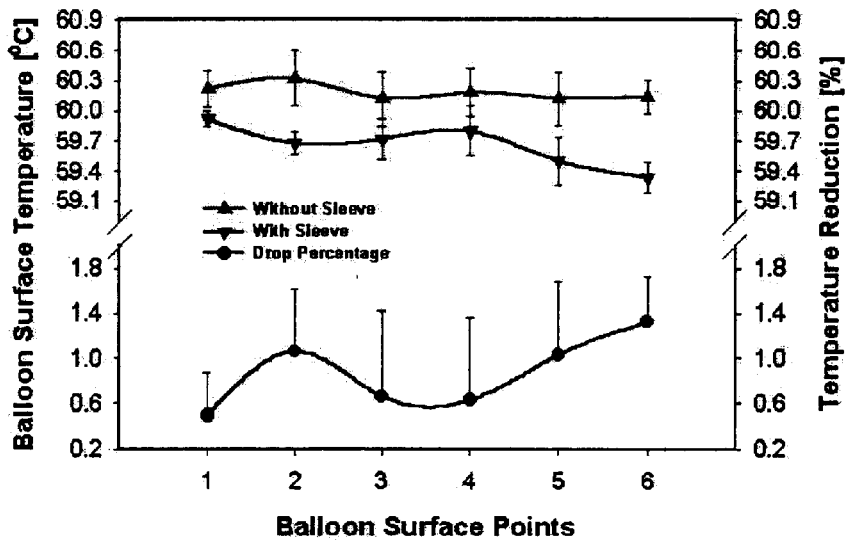
Figure 11B:
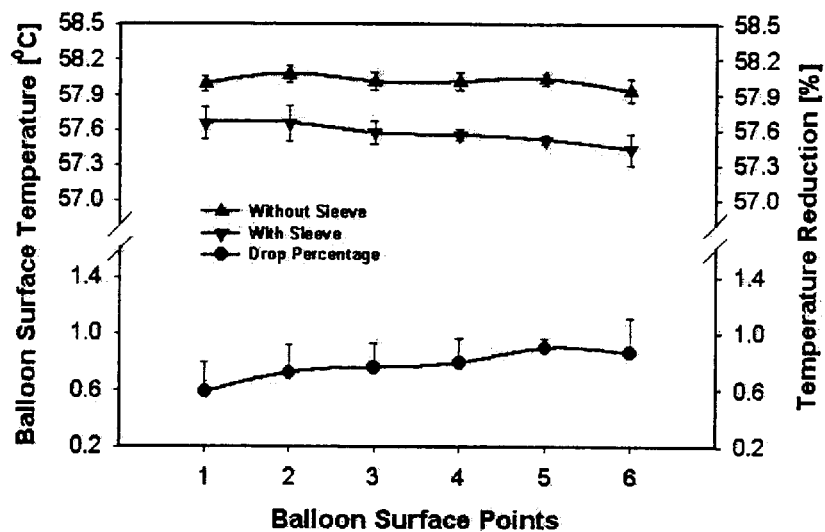
Figure 11C:
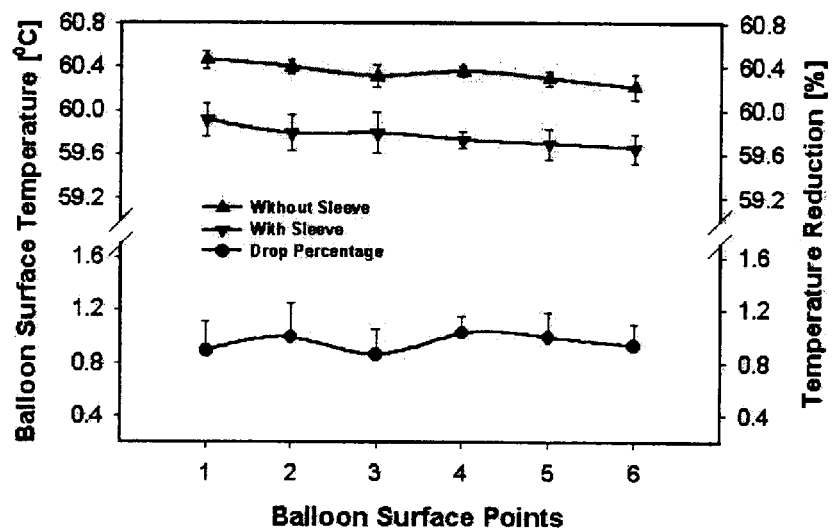

FIGS. 11A and 11C illustrate the same sleeve configuration shown in FIGS. 10A and 10C, but with a set temperature of at about 62 degrees Celsius. Again, less than a one-degree temperature loss is indicated. FIGS. 11A and 11C illustrate that for the first set of experiments at the 62 degree temperature setting (a) at position 1, about 0.9 degrees or 1.4% decrease, and (b) at position 2, about 0.6 degrees or less than about 1.0% decrease, compared to a sleeveless conventional catheter. It is anticipated that, in the body, the temperature drop will be even less. FIGS. 10B and 11B illustrate the temperature results for a thicker treatment balloon wall thickness and the same sleeve thickness of about 0.005 inches thick for position 1. FIG. 10B corresponds to the 60 degree C. temperature setting and FIG. 11B corresponds to the 62 degree C. temperature setting.

FIGS. 12A, 12B, 12C and 12D employed the same sleeve configuration and thicker wall treatment balloon as described for FIGS. 10B and 11B, and also include a quantity of petroleum jelly disposed intermediate the sleeve and the treatment balloon. FIG. 12C illustrates position 1 with the 62 degree C. set temperature and FIG. 12D illustrates position 1 with the 60 degree set temperature, each of FIGS. 12C and 12D show the percent drop and actual temperatures for petroleum jelly and sleeve and sleeveless configurations.

FIG. 12A illustrates position 1 for a 60 degree C. set temperature and FIG. 12B illustrates position 1 for a 62 degree C. set temperature. FIGS. 12A and 12B compare the temperatures for three configurations, with a sleeve, with a sleeve and petroleum jelly, and without the sleeve. As shown, the temperature actually increased in both sleeve with petroleum jelly cases at the outer surface of the sleeve (about 0.4–0.5 degrees) compared to the temperature of the sleeveless configuration at the treatment balloon surface.

FIGS. 13A and 13B illustrate the use of a thicker sleeve (four times thicker than that used for FIGS. 10–12) with petroleum jelly. The sleeve thickness used was 0.5 mm (0.020 inches). As shown, the temperature drop for the thicker sleeve with the petroleum jelly is less than one degree and less than 1.0% (about 0.7–0.8% depending on the set temperature).

FIGS. 14A and 14B illustrate the thicker sleeve (0.5 mm or 0.020 inches) but with a different fluid disposed between the treatment balloon and the sleeve. A viscous cream was used in this experiment. FIG. 14A is for the 60 degree C. set temperature and FIG. 14B for the 62 degree C. set temperature. More particularly, a medication cream known as FARCO-TRIL®, was used as described hereinabove. The sleeve with the medication cream did not experience a temperature drop, rather an increased surface temperature was measured (0.2–0.4 degree increase) at multiple points.

FIGS. 15A and 15B graphically illustrate the temperatures obtained with sleeveless configurations and with the 0.020 inch sleeves having either petroleum jelly or medication creams therein for the two different heat settings.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A catheter configured for insertion into a body lumen or cavity, comprising:
   a tubular body having an outer surface;
   an inflatable treatment or tissue molding balloon disposed over a portion of the outer surface of the tubular body configured to expand outwardly therefrom;
   a sleeve having a thickness of between about 0.005–0.030 inches disposed over the inflatable treatment or tissue molding balloon such that both are concurrently responsive to pressure introduced in the treatment or tissue molding balloon; and
   a quantity of a material disposed between the sleeve and the inflatable treatment balloon, wherein the sleeve and material have a low thermal resistance such that the temperature drop from the outer surface of the treatment balloon through the material to the outer surface of the sleeve is less than about 0.5 degrees.

2. The catheter according to claim 1, wherein the material is viscous or semi-viscous at ambient temperature.

3. The catheter according to claim 2, wherein the material comprises at least one bioactive or therapeutic agent.

4. The catheter according to claim 1, wherein the material is a cream at ambient temperature.

5. The catheter according to claim 1, wherein the material is gelatinous at ambient temperature.

6. The catheter according to claim 2, wherein the material comprises particulate matter.

7. The catheter according to claim 1, wherein the material changes its physical state when exposed to elevated treatment temperatures.

8. The catheter according to claim 1, wherein the material comprises a steroid.

9. A catheter configured for insertion into a body lumen or cavity, comprising:
   a tubular body having an outer surface;
   an inflatable treatment or tissue molding balloon disposed over a portion of the outer surface of the tubular body configured to expand outwardly therefrom to deliver thermal treatment to a subject;
   a sleeve having a thickness of between about 0.005–0.030 inches disposed over the inflatable treatment or tissue molding balloon such that both are concurrently responsive to pressure introduced in the treatment or tissue molding balloon; and
   a quantity of a viscous or semi-viscous therapeutic material at ambient temperature disposed between the sleeve and the inflatable treatment balloon to facilitate heat transfer from the inflatable treatment or tissue molding balloon to the subject, the material having a thickness of between about 1.0 mm to about 1.5 mm.

10. The catheter according to claim 9, wherein the material is formulated as a cream.

11. The catheter according to claim 9, wherein the material comprises a lubricant.

12. The catheter according to claim 9, wherein the material is gelatinous.

13. The catheter according to claim 9, wherein the material comprises at least one therapeutic or bioactive agent.

14. The catheter according to claim 9, wherein the therapeutic material comprises an anesthetic material.

15. The catheter according to claim 9, wherein the therapeutic material is selected for its ability, to treat urinary tract diseases, inflammation, or infections or to promote healing of damaged tissue in the urinary tract.

* * * * *